United States Patent [19]

Albrecht et al.

[11] Patent Number: 4,849,412
[45] Date of Patent: Jul. 18, 1989

[54] METHODS AND COMPOSITIONS FOR TREATING VIRAL INFECTIONS

[75] Inventors: Thomas Albrecht, Galveston; Chan H. Lee, Houston; Odd S. Steinsland, Galveston, all of Tex.

[73] Assignee: Board of Regents, The University of Texas System, Austin, Tex.

[21] Appl. No.: 944,301

[22] Filed: Dec. 19, 1986

Related U.S. Application Data

[63] Continuation-in-part of Ser. No. 871,120, Jun. 5, 1986, Pat. No. 4,800,081, which is a continuation-in-part of Ser. No. 601,471, Apr. 18, 1984, Pat. No. 4,663,317.

[51] Int. Cl.$^4$ ............... A61K 31/70; A61K 31/47
[52] U.S. Cl. ..................... 514/46; 514/49; 514/309; 514/934
[58] Field of Search ................ 514/46, 49, 309

[56] References Cited

U.S. PATENT DOCUMENTS 4,663,317  5/1987  Albrecht et al. .............. 514/211

FOREIGN PATENT DOCUMENTS 0109234  5/1984  European Pat. Off.
0235931  9/1987  European Pat. Off.

OTHER PUBLICATIONS

Albrecht, T. et al. (1984) "Cellular Responses to Human Cytomegalovirus Infection" in CMV; Pathogenesis and Prevention of Human Infection, Birth Defects: Original Article Series, vol. 20, No. 1.
Albrecht, T., Speelman, D. J. and Steinsland, O. S. (1983) Life Sciences, 32:2273.
Albrecht, T., Speelman, D. J., Nokta, M., and Steinsland, O. S. (1984) "Control of Cytomegalovirus Expression and Replication by Modification of the Cellular Response to Virus Infection" (Abstract).
Stanwick, et al. (1977), Infect. Immun. 18:342–347.
Lucas, et al. (1978), J. Exp. Med., 148:940–952.
Robbins, et al. (1980), Virology, 106:317–326.
Miller, et al. (1982), Proc. Natl. Acad. Sci., 79:1629–1633.
Grunberg, et al. (1970), Ann. N.Y. Acad. Sci., 173:122.
Tampieri, et al. (1980) Med. Biol. Environ., 8:199.
Tampiere, et al. (1981), Ann. Sclavo, 23:214.
Yoshikawa, et al, (1984), Jrnl. Virol., 50:489.
Nugent, et al, (1984), Arch, Virol., 81:163
Albrecht, et al, (1985), Abstract presented at the 10th International Herpes Visur Workshop.
International Search Report.
Shepp et al. (1985), Ann. Int. Med., 103:368–373.
Felenstein et al. (1985), Ann. Int. Med., 103:377–380.
Erice et al. (1987), JAMA, 257:3082–3087.
Laskin et al. (1987), Am. Jrnl. Med., 83:204–207.
Laskin et al. (1987), Jrnl. Inf. Dis., 155:323–327.

(List continued on next page.)

Primary Examiner—John W. Rollins
Attorney, Agent, or Firm—Arnold, White & Durkee

[57] ABSTRACT

The disclosure demonstrates the inhibition of replication of human cytomegalovirus (HCMV) in cultured human embryo skin muscle cells by two separate subclasses of direct-acting smooth muscle relaxing agents alone or in combination with each other. These two subclasses are characterized mechanistically as calcium influx blockers (or calcium channel blockers) and cyclic nucleotide modulators. More specifically, the class of calcium influx blockers is exemplified by the drugs verapamil (and methoxyverapamil), nifedipine (the prototype drug of 1,4 dihydropyridines), and diltiazem. The class of cyclic nucleotide modulators is exemplified by the drugs isobutylmethylxanthine, papaverine (and its synthetic analog dioxyline), forskolin, and sodium nitroprusside. In addition, the present disclosure demonstrates that agents from one class, e.g., a calcium influx blocker, act synergistically when used in combination with agents from the other class, e.g., cyclic nucleotide modulators. The calcium influx blockers are shown to act synergistically when used in combination with alpha interferon. In further embodiments, papaverine family member agents are shown to exert antiviral activity synergistically with antiviral nucleoside analogs.

8 Claims, 12 Drawing Sheets

OTHER PUBLICATIONS

International Search Report.
"Clarke's Isolation and Identification of Drugs" (1986), 2nd Edition, Moffat et al., Ed's, pp. 848-849.
"Disposition of Toxic Drugs and Chemicals in Man" (1982), 2nd Edition, Baselt, ed.
Albrecht et al. (1987), *Proc. Soc. Exp. Biol. Med.*, *186:41-46.*
Duke et al. (1986), *Antiviral Res.*, 6:299-308.
Koretz et al. (1986), *New Eng. J. Med.*, 314:801-805.
Freitas et al. (1985), *Antimicrob. Agents Chemother.*, 28:240-245.
Smee et al. (1983), *Antimicrob. Agents Chemother,* 23:676-052.
Mar et al. (1983), *Antimicrob. Agents Chemother.*, 24:518-521.
Masur et al. (1986), *Annals of Int. Med.*, 104:41-44.
Elion et al. (1977), *Proc. Natl. Acad. Aci., U.S.A.,* 74:5716-5720.
Erice et al. (1987), *Jrnl. Am. Med. Assoc.,* 257:3082-3087, (Abstract only).

METHODS AND COMPOSITIONS FOR TREATING VIRAL INFECTIONS

The government may own rights in the present invention pursuant to NIH contract NO1-AI42557.

BACKGROUND OF THE INVENTION

The present application is a continuation-in-part of application Ser. No. 871,120, filed June 5, 1986, now U.S. Pat. No. 4,800,081, which is a continuation-in-part of application Ser. No. 601,471, filed Apr. 18, 1984, now U.S. Pat. No. 4,663,317.

The present invention relates to methods and compositions for treating viral infections. More specifically, the invention is directed towards the treatment of viral infections through the use of smooth muscle relaxing agents and agents that block the entry of calcium ions ($Ca^{++}$) into cells. These agents appear to act by blocking replication of the target viruses in infected cells.

Advances in the treatment of viral infections have been very slow in coming. Very few efficacious antiviral agents presently exist. A few agents have been touted for their potentially specific antiviral activity are in the research and development stage. The clinical efficacy of these agents, such as interferon and interferon inducers (e.g., polyanionic pyran copolymers and double stranded RNA) have yet to be reproducibly demonstrated.

A few pharmaceutical agents have shown promise in the treatment of isolated viral infections, including the use of amantadine in the treatment of Influenze $A_2$ strains. The use of the antimetabolities, Idoxuridine and Cytarabine, in antiviral therapy is hampered by a narrow spectrum of activity and potentially severe side effects. Methisazone is receiving some support for its use against some pox and vaccinia strains. Its use in pox infections is generally limited to prophylaxis. In general, there are presently no efficacious antiviral agents that demonstrate a broad spectrum of activity. It now appears that no single broad spectrum agent, or family of agents, may be identified as useful in antiviral treatment. Therefore, research is being directed towards identifying antiviral agents with activity against selected viral diseases.

A novel approach to the treatment of certain viral diseases, including human cytomegalovirus (HCMV), varicella zoster virus, and herpes simplex virus, is addressed by the present invention. This approach involves the restriction of viral expression and replication in infected cells by controlling and modifying the cellular responses to viral infection.

HCMV causes acute and apparently life-long persistent infections of man (T. H. Weller, N. Eng. J. Med. 285: 203-214, 267-274 (1971)). HCMV infection has been determined the causative agent in a number of birth defects, including microencephalopathy, hydroencephalopathy and microthalmia. Other defects associated with pre-natal HCMV infections include severe mental retardation, disordered hepatic function, and hyperbilirubinemia. Although the disease is often asymptomatic in children and adults, HCMV infections in these groups have been shown to result in enlargement of the liver and spleen and deranged erythropoesis. The disease may remain dormant for years, then reactivated by unknown causes. Localized and generalized HCMV infections have been shown to develop after immuno-suppressive and anti-neoplastic therapy. HCMV is a member of the herpes family of viruses.

The most widely recognized feature of HCMV-induced cytopathology is the formation of distinct nuclear and cytoplasmic inclusions (CI's) (T. Albrecht, T. Cavello, N. L. Cole, and K. Graves, Lab. Invest., 42: 1-7 (1980)). Another HCMV cytopathic effect involves the rounding of fibroblastic cells beginning within the first several hours after infection. By 12-24 hours post-infection, depending on the intensity of the infection, nearly all cells are small and rounded.

The novel approach to restrict virus expression and replication presented by the present invention is to control the cellular response to virus infection. Such approaches may be particularly warranted for human cytomegalovirus since this virus is an important cause of disease for which effective therapeutic agents have not yet been identified. Additionally, as previously noted, HCMV infections present notable changes in cytopathology which suggest that cytopathic-directed therapy might prove particularly efficacious in the treatment of that disease.

SUMMARY OF THE INVENTION

A method is provided for the treatment of human viral diseases, in particular HCMV and HSV, through the use of drugs heretofore unknown to possess antiviral activity. These agents can be classified in a broad sense as direct-acting smooth muscle relaxing agents. Two sub-classes of the direct-acting smooth muscle relaxing agents, the calcium influx blockers and cyclic nucleotide modulators, are shown to have antiviral activity.

In particular, a method for treating viral infections in an infected host is presented wherein the method includes administering to the host an effective amount of a calcium influx blocker in combination with an effective amount of a cyclic nucleotide modulator. Calcium influx blockers are generally represented by the 1,4 dihydropyridines, the verapanoids and diltiazem. The cyclic nucleotide modulators are generally represented by the agents, isobutylmethylxanthine, papaverine, dioxyline, sodium nitroprusside, and forskolin. These agents were chosen as representative agents for their particular chemical structural class. For example, sodium nitroprusside is representative of those smooth muscle relaxing agents known as the nitrates. Similarly, the verapanoids are represented by, for example, verapamil and methoxyverapamil. Similarly, the drug nifedipine is representative of the class of 1,4 dihydropyridines.

In a further aspect of the present invention, a method for treating viral infections in an infected host is disclosed which includes administering to the host an effective amount of alpha interferon in combination with an effective amount of a calcium influx blocker. This combination also demonstrates synergistic antiviral activity over and above either one of these agents antiviral activity when used alone.

The antiviral methods of the present invention may conveniently be performed utilizing a pharmaceutical composition which comprises an effective amount of a calcium influx blocker, or a pharmaceutically acceptable salt thereof, in combination with an effective amount of a cyclic nucleotide modulator, or a pharmaceutically acceptable salt thereof. Such compositions may further include the addition of an effective amount of alpha interferon. Interferon-containing compositions, however, may simply include the alpha interferon in combination with an effective amount of a calcium influx blocker.

In still further aspects of the present invention, a method for treating viral infections in an infected host is disclosed which includes administering to the host an effective amount of a synthetic nucleoside analog, for example, DHPG (9-(1,3-dihydroxy-2-propoxymethyl)-guanine), or pharmaceutically acceptable salts thereof, together with an effective amount of a papaverine family agent having an available isoquinoline ring nitrogen (e.g.--papaverine, dioxyline, ethaverine or tetrahydropapaverine), or pharmaceutically acceptable salts thereof. This combination, particularly where papaverine is the selected papaverine family agent, demonstrates surprising synergistic antiviral activity over and above either one of these agent's antiviral activity when used alone.

Moreover, studies are disclosed which suggest that papaverine, one of the cyclic nucleotide modulations, is acting mechanistically as an antiviral agent through inhibiting the release of intracellular free calcium from intracellular calcium stores. The demonstrated ability of papaverine to inhibit intracellular calcium release further suggests that this agent, acting alone or in combination with other agents, may have practical value in the control of virus infections, immune responses, and cell proliferation such as occurs in cancer. Cytosolic $Ca^{++}$ responses are important in the activation of immune cells, the control of initiation of proliferation of other cells including cancer cells, and the replication of viruses. Therefore, papaverine, and related drugs, through its inhibition of the $Ca^{++}$ response which is associated with immune cell activation, cancer, and other cell proliferation and virus replication may have therapeutic value where these activities are involved.

DETAILED DESCRIPTION OF THE PREFERRED EMBODIMENTS

Figure 1:
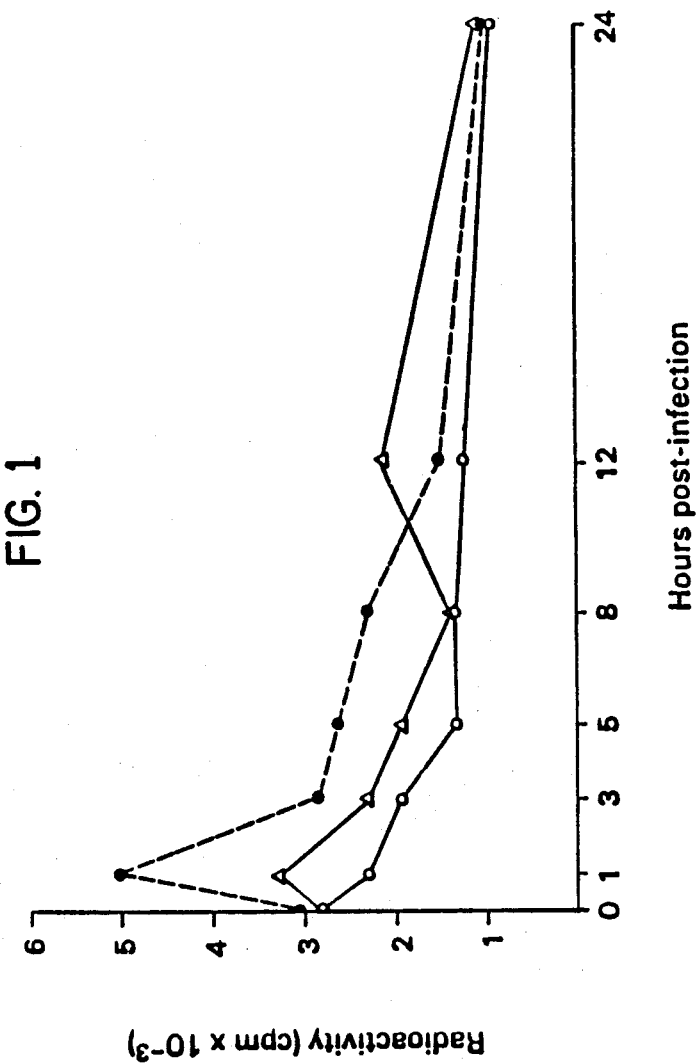
FIG. 1 demonstrates the total $^{45}CaCl_2$ accumulated by CMV-infected cells (●--●), CMV-infected cells in presence of 30 ug/ml verapamil (△--△), and uninfected (O----O) THY (a human fibroblast cell line) cells. Tightly confluent monolayers were infected at a MOI (multiplicity of infection) of 3 PFU/cell. After 1 h absorption, the virus was decanted and EMEM (Eagle's modified essential medium) with 5% FCS was added. At different times, post infection, the cells were labeled with $^{45}CaCl_2$ 1 uCi/ml for 3 min. The labelling media was then removed and cells were washed twice with ice-cold isotonic sucrose (8.75% w/v). Then cells were extracted with 1 ml of 0.1N NaOH added to each dish for 2 h. Radioactivity was measured with a Beckman scintillation counter.

In its most general and overall scope, the present invention embodies the realization that viral infections may be successfully treated through the inhibition of cellular calcium fluxes. The antiviral agents of the present invention appear to act through calcium flux inhibition which, in turn, serves to block viral replication. This viral replication can most readily be visualized in the case of HCMV infections where viral infection is accompanied by a characteristic, readily observable, morphologic cascade. The sequence of the cellular responses exhibited upon HCMV infection is rounding, "contraction," "relaxation," and enlargement. Rounding of cells begins before 5 hours post-infection (PI) when cells in intermediate stages of rounding are observed, and continues through 12 to 24 hours PI. At this time the population of those rounded cells with the smallest size is similar in diameter to that of the nucleus of uninfected cells. By 48 hours PI most infected cells have "relaxed," partially flattened, and begun to enlarge. At later times, HCMV-infected cells are observed to be much enlarged. Inhibition of early cellular responses to HCMV infection is achieved by Ca++ influx blockers and other smooth muscle relaxing agents.

The present invention utilizes drugs which inhibit the observed morphologic cascade which cells undergo during HCMV infection. The initial response of the cells to HCMV infection, cell rounding, is mediated by the activation of contractile elements within the cell. Likewise, cellular control of these contractile elements is mediated by changes in the intracellular concentration of calcium ions. More specifically, numerous cellular responses to ear;y viral infection are consistent with a rise in intracellular free Ca++. Thus, these morphologic responses could be related to a change in plasma membrane permeability and a concomitant Ca++ influx.

Thus, in certain aspects, the present invention embodies the realization that viral infections may be treated by correcting for symptomatic changes in cellular morphology. The successful use of smooth muscle-relaxing agents in reversing the cell rounding induced by HCMV is demonstrated by direct microscopic examination of infected cells after drug treatment. A concomitant inhibition of viral replication is demonstrated by fold reductions in viral plaque forming units being released from treated cells.

The antiviral agents of the present invention appear to act by either inhibiting the influx of extracellular calcium into infected cells (i.e., the calcium influx blockers) or by inhibiting the flux of calcium intracellularly from intracellular calcium "pools". In CMV infected cells, calcium flux inhibition of either variety results in the observed return to morphologic normally. In treating viral infections which do not effect similar cellular morphologic changes, (for example, as in measles, influenza and HTLV III (AIDS) infections) there, of course, is no readily observable morphologic reversion as in the case of CMV. However, the fact that the present agents are active in either case suggests the possibility that calcium sensitive antiviral targets may exist in addition to, or in combination with calcium sensitive morphologic structures.

Smooth muscle relaxing agents exert their activity by both indirect (e.g., through modification of smooth muscle nerve transmissions) and direct (i.e., through direct action on the cells) actions. The indirect-acting smooth muscle relaxing agents are represented by a wide variety of agents exhibiting great variations in mechanisms of action. These indirect-acting smooth muscle relaxing agents have not been tested for activity in inhibiting virus replication in infected cells.

Two classes of direct-acting agents, the calcium influx blockers (also referred to as calcium channel blockers) and cyclic nucleotide modulators, as a group demonstrate very high inhibition of viral replication in infected cells.

The calcium influx blockers are represented by three general chemical classes of agents: (1) the 1,4 dihydropyridines (of which the prototype drug is nifedipine), (2) a second class, the verapanoids, which includes verapamil and methoxyverapamil, and (3) a third class characterized by the drug diltiazem.

The smooth muscle relaxing agents that exert their action via modulation of intracellular cyclic nucleotide levels are generally classified as to whether or not they affect the enzyme, phosphodiesterase. Phosphodiesterase is the enzyme responsible for metabolism of cyclic nucleotides. The most effective cyclic nucleotide modulators, in terms of inhibiting viral replication, are represented by the agents papaverine, and dioxyline, a synthetic compound that is both chemically and pharmacologically very similar to paparevine. The second class of smooth muscle relaxing cyclic nucleotide modulators exert their activity through poorly understood mechanisms other than through inhibition of phosphodiesterase. This class includes the agents forskolin and sodium nitroprusside.

However, further evidence suggests that papaverine may alternatively or additionally be acting by a second mechanism other than cyclic nucleotide modulation. This second mechanism is by inhibition of intracellular calcium fluxes, i.e., by inhibiting the release of intracellular free calcium from intracellular calcium stores. In particular, it is shown that effective antiviral treatment may be obtained with papaverine at concentrations that do not result in the inhibition of phosphodiesterase activity, i.e., at papaverine concentrations that do not affect intracellular cyclic nucleotide levels.

Treatment of virtually infected cells with a combination of smooth muscle relaxing agents in accordance with the present invention can provide a greatly enhanced antiviral efficacy when compared to treatment with individual agents. In particular, treatments with a combination of a cyclic nucleotide modulator (e.g., papaverine) with a calcium influx blocker (e.g., verapamil or nifedipine) demonstrate surprising synergistic effects. Administered alone, verapamil (30 uM) resulted in a 10-fold inhibition and papaverine (5 uM) resulted in an 18-fold viral inhibition. However, when administered in combination at the same concentrations, these agents provided a 112-fold inhibition of viral yields. For the purposes of the present invention, it was felt that the best evidence available to demonstrate these agents activity in humans was by demonstrating their ability to inhibit viral replication and production in infected human cells in culture.

Moreover, treatment of virtually infected cells with papaverine in combination with DHPG (dihydroxy propoxymethyl guanine), a synthetic nucleoside analog, has been shown to demonstrate surprising synergistic antiviral efficacy. For example, when administrated alone to CMV infected cells, papaverine, at 1.5 uM, resulted in approximately an 8.7-fold inhibition of virus yields over controls. DHPG, when administered alone to similarly infected cells at a concentration of 3 uM, resulted in approximately a 72-fold inhibition of viral yields. However, when administered in combination at these same concentrations, these agents provided a 3000-fold inhibition over controls.

Although it is contemplated that the present invention may be successfully utilized to treat numerous types of viral infections, including those caused by the RNA and DNA viruses, the invention is herein disclosed in terms of its particular efficacy in inhibiting CMV and herpes virus infections, both HSV-1 and HSV-2. These viral infections, in addition to presenting a formidable health problem for which few efficacious agents are present available, present a useful model system for identifying those agents which exert their antiviral activity through modulation of calcium levels. Thus, the morphologic changes associated with CMV infection of cells, and the resultant morphology which accompanies CMV inhibition, provides a useful, readily observable indicator of antiviral activity. However, the efficacy of the present agents in treating viral infections which do not exhibit a similarly striking morphologic cascade, e.g., the measles, influenza and HCMV III viruses, suggests that the morphologic effects observed in the treatment of CMV-infected cells may be secondary to, or in addition to, the underlying antiviral mechanism.

In a typical protocol, human embryo skin muscle cells are first grown to confluency in Leighton tubes in 1 ml. of Eagle's media supplemented with Earle's salts, 10% fetal calf serum (FCS), and 0.75% sodium bicarbonate. This requires approximately 2-4 days growth. At the end of this time, the tubes contain about $2 \times 10^5$ cells. Once confluent, the growth media is removed and 0.3 ml. of the virus stock is placed onto the cells (5 pfu/cell) and allowed to adsorb for 1 hr. at 37° C. The virus stock is aspirated off and the cell monolayer washed twice with maintenance media (Eagle's MEM supplemented with Earle's salts, 5% FCS, and 0.15% sodium bicarbonate). The last wash is replaced with 1 ml. of fresh maintenance media containing the indicated drug concentration. The drug is always made up fresh.

The cells are generally treated with drug for a total of 120 hours. In some experiments, the drug-containing media is replaced every 24 hrs., and in others, every 48 hrs. This variation has no effect on the results.

To test the level of virus replication during drug treatment, the treated cells are quick-frozen in a Revco −70° C. freezer, then put through two freeze/thaw cycles. The cell-containing tubes are then sonicated in a "bath" sonicator for 45 seconds. The cell lysates are assayed for infectivity by a standard plaque assya. (Albrecht, T. and Weller, T. H., *Am. J. Clin. Path.*, 73: 648-651 (1980)). The following table (Table 1) depicts the results of initial experiments which demonstrated activity of the smooth muscle relaxing agents in inhibiting HCMV replication using the foregoing protocol.

TABLE 1

Inhibition of HCMV Replication by Smooth Muscle Relaxing Agents*

| Drug | Dose (ug/ml) | % Inhibition of Virus Yield | Fold Inhibition |
|---|---|---|---|
| Verapamil | 1 | 44.4 | 1.8 |
|  | 3 | 27.8 | 1.4 |
|  | 10 | 78.3 | 4.6 |
|  | 30 | 83.3 | 6.0 |
| Nifedipine | 1 | 34.7 | 1.5 |
|  | 3 | 56.1 | 2.3 |
|  | 10 | 93.0 | 14.3 |
|  | 30 | 99.9 | 1000 |
| Isobutyl-methylxanthine (IBMX) | 30 | 44.0 | 2.27 |
| Papaverine | 1 | 97.2 | 35.7 |
|  | 3 | 99.98 | 5000 |
|  | 10 | 99.995 | 20000 |
|  | 30 | 99.998 | 50000 |
| Forskolin | 1 | 40.9 | 1.7 |
|  | 3 | 54.5 | 2.2 |
|  | 10 | 88.2 | 8.5 |
| Sodium Nitroprusside | 1 | 45.5 | 1.8 |
|  | 3 | 45.5 | 1.8 |
|  | 10 | 60.0 | 2.5 |
|  | 30 | 99.3 | 143 |

*multiplicity of infection = pfu/cell

Further tests of the smooth muscle relaxing agents against two types of herpes simplex virus (HSV-1 and HSV-2) demonstrate the usefulness of the present invention in inhibiting the replication of herpes virus. The particular strain of HSV-1 utilized was KOS and HSV-2 was 198. The activity of the agents against HSV was determined in the same manner as described above for CMV. Both of the viral strains were grown in human embryo skin muscle cells in culture and the infected cells were then transferred to mecia containing 30 ug/ml of the indicated agent and the PFU determined at 24 hours PI. These results are compiled in the following table (Table 2).

TABLE 2

| | % Inhibition of Virus Yield | |
|---|---|---|
| Drug | HSV-1 | HSV-2 |
| Verapamil | 96.1 | 95.8 |
| Papaverine | 86.1 | 67.7 |
| Sodium Nitroprusside | 0 | 53.8 |

Inhibition of HSV-1 and HSV-2 by Smooth Muscle Relaxing Agents*

*multiplicity of infection = 5 pfu/cell

The discussion and experimental examples which follow, provide a more in-depth disclosure of the present invention and is meant to provide those of skill in the art with a greater understanding and appreciation of the mechanistic antiviral function of the agents presently disclosed.

A. Inhibition of the cellular response to cytomegalovirus infection

1. Sequence of cellular responses to CMV infection

Following human embryonic fibroblasts infection with CNV and other viruses, the infected cells demonstrate a progression of cytopathic effects (Albrecht et al., 1983), beginning with rounding of the cells by 5 hours post-infection (PI). In the course of rounding, the cells assume an intermediate form, which raised the possibility that these cells might be undergoing a contractile-like response. This concept was supported by the finding that the rounded cells decreased in diameter until at 24 h PI the cells with the smallest size were approximately the size of the nucleus of uninfected cells. By 48 h PI, the cells "relax," flatten, and enlarge. During the next several days, the cells progressively enlarge and develop the nuclear and cytoplasmic inclusions characteristic of viral infection.

2. "Relaxation" and cytomegaly do not require CMV DNA synthesis

In cytomegalovirus infected cells, DNA synthesis begins between 12 and 16 h PI. Thus, rounding and "contraction" of CMV-infected cells (beginning before 5 h PI) are, by definition, early events in the virus replication cycle, since they occur before the onset of virus DNA synthesis; "relaxation" and enlargement are presumably "late" events, since they occur only after the time of onset of virus DNA synthesis. To determine if "relaxation" and enlargement required CMV DNA synthesis, SM cells were infected and then treated with 30 ug/ml of cytosine arabinoside (Ara-C) which blocks virus DNA synthesis. Ara-C failed to block either "relaxation" or enlargement. These data indicate that cytomegaly, although a late event, does not require virus DNA synthesis and is the result of early CMV gene expression.

3. The effect of $Ca^{++}$ influx blockers on the development and progression of cytomegaly and nuclear inclusions The previous study demonstrated that late cellular responses to CMV infection such as "relaxation" and cytomegaly, did not require late CMV gene expression. Since early cellular responses such as rounding and "contraction" are inhibited by $Ca^{++}$ influx blockers (e.g., verapamil, nifedipine), it was possible that late responses would also be inhibited by these drugs. Treatment of CMV-infected cells with either verapamil or nifedipine at 5 h PI inhibited late cellular responses. In verapamil-treated cells, NIs were present in most nuclei, although their size was reduced relative to untreated controls. These data indicate that the development and progression of CMV NIs are dependent on a $Ca^{++}$ influx as are other cellular responses to CMV infection.

4. The effect of cyclic nucleotide modulators on the development and progression of CMV-induced late cellular responses The effect of cyclic nucleotide modulators on the development and progression of cytomegaly and NIs was measured by microscopic examination of CMV-infected, H&E-stained SM (hyman embryo skin muscle cells) or THY cells. The cyclic nucleotide modulating drugs were added at 5 h PI which permitted early CMV-induced cellular responses such as cell rounding and "contraction" to occur. As displayed in Table 3, cyclic nucleotide modulating drugs added at 5 h PI inhibited "relaxation," development of cytomegaly, and the formation and progression of NIs measured at 48 and 72 h PI. These drugs, which are well recognized for increasing the concentration of cAMP and/or cGMP in other tissues, were potent inhibitors of late cellular responses to CMV infection.

TABLE 3

Inhibition of CMV-Induced Cytomegaly and Nuclear Inclusions by Cyclic Nucleotide Modulators

| | Effect on Cyclic Nucleotides[3] | | Inhibition of Cellular Responses[4] | | |
|---|---|---|---|---|---|
| Treatment[2] | cAMP | cGMP | Relaxation | Cytomegaly | Nuclear Inclusion |
| Papaverine | [ ] | [ ] | +++ | ++++ | ++++ |
| IBMX | [ ] | [ ] | ++ | +++ | ++++ |
| Forskolin | [ ] | | ++++ | ++++ | ++++ |
| Nitroprusside | | [ ] | — — | — — | +++ |

[1]MOI = 5 PFU/cell.
[2]A dose of 3 × 10$^{-5}$ g/ml of each drug was used. All drugs were added at 5 h PI.
[3]This information is derived from studies in other tissues. [ ], increased concentration.
[4]Determined at 48 and 72 h PI. +, 1–25% inhibition; ++, 26–50% inhibition; +++, 51–75% inhibition; ++++, 76–100% inhibition; —, no inhibition.

B. $C^{++}$ responses to CMV infection

1. The effect of CMV on $Ca^{++}$ fluxes in human fibroblasts

Measurement of $^{45}Ca^{++}$ in infected and mock-infected cells following a 30 min. incubation period in media containing $^{45}CaCl_2$ (1 uCi/ml), suggested that intracelluar [$Ca^{++}$] increases in CMV-invected cells by 1 h post-infection (FIG. 1). This $Ca^{++}$ influx declined by 3 h PI. Significant differences in $^{45}Ca^{++}$ influx were not noted between the virus-infection and the control cells from 12 to 24 h PI. This influx was significantly inhibited in the presence of 30 ug/ml of verapamil. Although these results were reproducible, the experimental data were dependent on several variables. As the multiplicity of infection (MOI) was deceased, the time at which the maximum $^{45}Ca^{++}$ influx occurred was delayed and the amount of radioactivity was decreased. For example, at a multiplicity of 1 PFU/cell, the maximum influx was observed at 8 h PI. If the control cells were stimulated at 0 h by replacing the cell lysate with fresh rather than spent medium, then a $^{45}Ca^{++}$ influx was also observed in the control cells. Although the influx obtained under these altered conditions occurred at the same time in infected and control cells, the magnitude of the influx in infected cells was about 2-fold greater.

2. Sequestering of $Ca^{++}$ in CMV-infected cells

Figure 2:
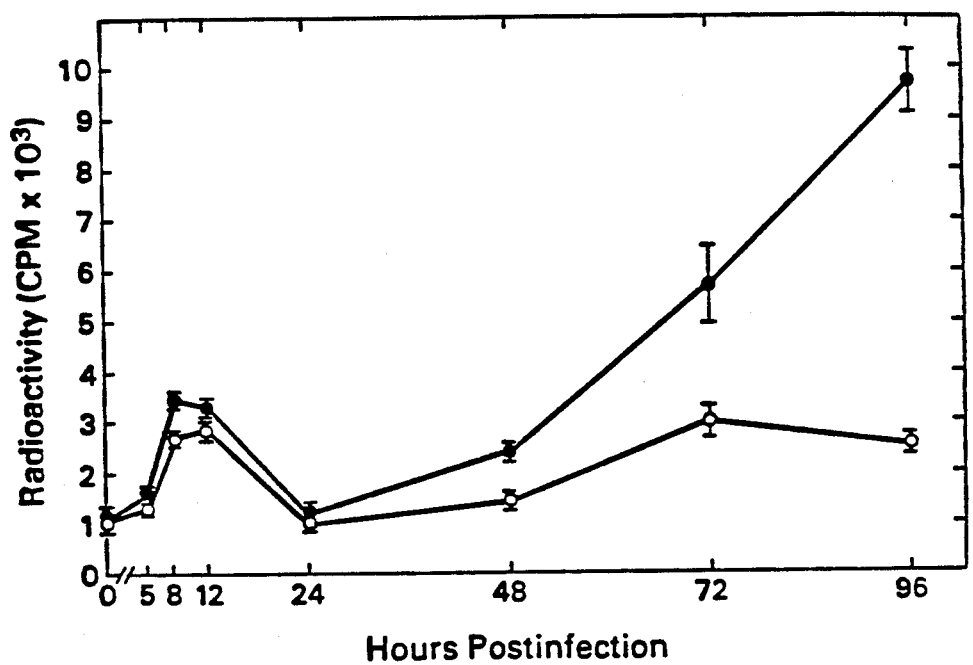
FIG. 2 illustrates the intracellular sequestering of $^{45}Ca^{++}$ in AD169-infected (3 PFU/cell) (--●--) and mock-infected (--o--) THY cells continuously labelled with $^{45}CaCl_2$ (1 uCi/ml: specific activity, 27.68 mCi/mg). Each datum point represents the mean of the determinations for 3 independent cultures processed separately, ± standard error of the mean.

The ability of CMV to increase the amount of $Ca^{++}$ sequestered in TCA-precipitable macromolecules was examined over a similar time interval. A rapid and substantial increase in $^{45}Ca^{++}$ radioactivity associated with the TCA-precipitable fraction of infected cells was observed (FIG. 2). These data indicate that CMV is able to increase total cellular and bound cellular $Ca^{++}$ early after infection.

3. Effect of CMV on intracellular free (IF) $[Ca^{++}]$

Figure 3:
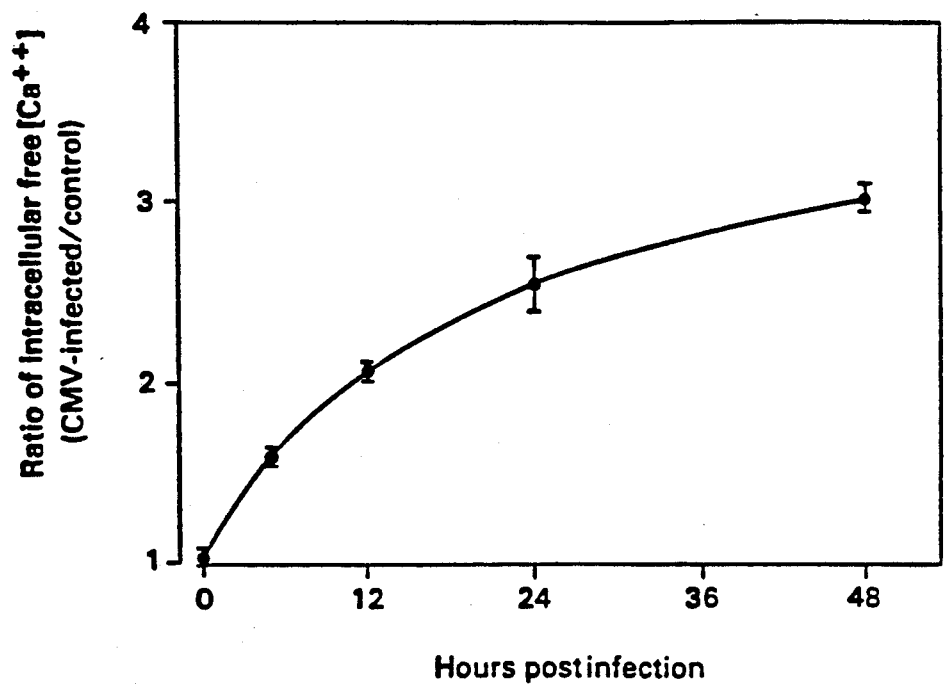
FIG. 3 demonstrates the intracellular free $[Ca^{++}]$ response to CMV infection. Confluent monolayers of THY cells were infected with CMV (strain AD-169) at a MOI of 3-5 PFU/cell for 1 h. At selected intervals, the medium was aspirated and the cells were incubated for 1 hr in EMEM containing 60 ug/ml of Quin-2 AM at 37° C. The cells were washed with PBS and removed from the flasks with 0.25% trypsin, pelleted, washed twice, and resuspended in a buffer containing 140 mM NaCl, 5 mM $KCL_2$, 20 mM HEPES, 10 mM glucose, 1 mM $MgCl_2$. The fluorescence was measured with a spectrophotofluorometer at emission and excitation wavelengths of 339 and 492 nM, respectively. Titration of free $Ca^{++}$ activity and computer analysis of the data were done. Each datum point represents the mean of the determinations for three or more independent cultures processed separately, ± the standard error of the mean.

Since many cellular mechanisms are regulated by changes in the intracellular levels of "free" calcium (IF $[Ca^{++}]$), the IF $[Ca^{++}$ in infected and uninfected cells were measured using the fluroescent $Ca^{++}$ indicator, Quin-2. Quin-2 fluorescence increased by about 100% as early as 12 h PI, indicating a large increase in IF $[Ca^{++}]$. This rise continued and then leveled off by 24 h PI (FIG. 3) at which time the fluorescence of infected cells was approximately 3 times more than in uninfected cells.

4. Relationship of CMV gene dosage to IF $[Ca^{++}]$

To determine the effect of CMV gene dosage on the CMV-induced increase in IF $[Ca^{++}]$, cells were infected with different multiplicities of infection (MOIs) (10, 3.5 and 1 PFU/cell). The increase in fluorescence units (FU) in infected cells relative to the control cells by 24 h PI was 67.5, 45.8 and 20.7 percent, respectively (Table 4). As the FU are proportional to the IF $[Ca^{++}]$, these results indicate that the increase in the CMV-induced IF $[Ca^{++}]$ is dependent on the virus gene dosage.

TABLE 4

| Effect of the CMV Gene Dosage on Intracellular Free $[Ca^{++}]$ | | |
|---|---|---|
| Sample | Fluorescence units* | Percent change |
| Uninfected cells | 38.6 | |
| CMV-infected cells (10 PFU/cell) | 64.6 | +67.5 |
| CMV-infected cells (3.5 PFU/cell) | 56.3 | +45.8 |
| CMV-infected cells (1 PFU/cell) | 46.6 | +20.7 |

*24 hour postinfection.

5. Effect of metabolic inhibitors and CMV-inactivation on the CMV-induced IF $[Ca^{++}]$ response It was additionally determined that active CMV was required for the observed increase in the IF $[Ca^{++}]$. Thus, when CMV was inactivated by heat (56° for 1 h), preincubation with CMV-specific antisera (37° C. for 1 h), or exposure to UV light ($7.2 \times 10^4$ ergs/mm$^2$), the fluorescence was less than that obtained with control cells infected with untreated CMV stock. Inhibition of the fluorescence increase by CMV inactivation was 96, 60 and 74 percent, respectively, at 24 h PI (Table 5). The inhibition of the fluorescence increase by CMV-inactivation indicates that the CMV-induced increase in IF $[Ca^{++}]$ is dependent upon a viable CMV genoma. As shown in Table 5, cycloheximide (10 ug/ml) inhibited the CMV-induced Quin-2 fluorescence increase by 84%. Cordycepin (20 ug/ml), an inhibitor of mRNA polyadenylation, had a similar effect, inhibiting the increase in IF $[Ca^{++}]$ by 62%. Thus, protein synthesis and competent mRNA were also required for the induction of the increase in IF $[Ca^{++}]$.

TABLE 5

Summary of the Effects of Metabolic Inhibitors and CMV Inactivation on Intracellular Free $[Ca^{++}]$ in Human Embryonic Thyroid Cells

| Cytomegalovirus[1] | Treatment | Fluorescence units[2] | % change of fluorescence | % inhibition of fluorescence change |
|---|---|---|---|---|
| Experiment 1 | | | | |
| − | None | 41 | | |
| + | None | 92 | 110 | |
| + | 3-deoxyadenosine[3] | 54 | 3 | 79 |
| − | 3-deoxyadenosine | | | |
| Experiment 2 | | | | |
| − | None | 42 | | |
| + | None | 79 | 88 | |
| + | Cycloheximide[4] | 48 | 14 | 84 |
| − | Cycloheximide | | 9.5 | |
| Experiment 3 | | | | |
| − | None | 26 | | |
| + | None | 49 | 88 | |
| + | Virus stock heated to 56° for 1 h before infection | 27 | 4 | 96 |
| Experiment 4 | | | | |
| − | None | 42 | | |
| + | None | 72 | 71 | |
| + | Virus stock reacted with CMV-specific serum[5] | 54 | 29 | 59 |
| + | Virus stock | 73 | 74 | −4 |

TABLE 5-continued

Summary of the Effects of Metabolic Inhibitors and CMV Inactivation on Intracellular Free [Ca$^{++}$] in Human Embryonic Thyroid Cells

| Cytomegalovirus[1] | Treatment | Fluorescence units[2] | % change of fluorescence | % inhibition of fluorescence change |
|---|---|---|---|---|
| | reacted with VZV-specific serum[6] CMV specific serum | 43 | 2 | |
| Experiment 5 | | | | |
| − | None | 56 | | |
| + | None | 75 | 34 | |
| + | Inactivation of virus stock with UV-light | 60 | 7 | 79 |

[1]MOI = 3 to 5 PFU/cell
[2]Measured at 24 h PI
[3]20 ug/ml added to cultured THY cells at 0 h PI
[4]10 ug/ml added to cultured THY cells at 0 h pI
[5]Human convalescent serum CMV positive, VZV-positive by immunofluorescence and complement fixation assays.
[6]Human convalescent serum CMV-negative, VZV positive by immunofluorescence and complement fixation assays.
[7]7.2 × 10$^4$ erg/mm$^2$.

6. The phase of CMV expression responsible for induction of increased IF [Ca$^{++}$].

Experimental results suggested that the Ca$^{++}$ influx occurred early in the replication cycle of CMV. The increase in IF [Ca$^{++}$] and the morphologic cellular response also appear to begin at early times. To more precisely determine the phase of CMV gene expression responsible for the IF [Ca$^{++}$] response (increase), protein synthesis was blocked in infected cells with cycloheximide (CH) and then the cells were released from the translational block in the presence or absence of a "transcription block" (3'-deoxyadenosine). Data from representative experiments are summarized in Table 6. At 24 h PI, about 54% more fluorescence was observed in infected than in noninfected cells. Addition of CH from 0-6 h PI reduced the increase in fluorescence to about 27%. The presence of 3'-deoxyadenosine from 6 to 24 h PI did not appreciably affect the level of fluorescence beyond that expected were transcription of a gene begins in the immediate early phase and continues into the early phase, suggesting that the increase in intracellular free Ca$^{++}$ was the result of immediate early CMV gene expression.

TABLE 6

Phase of CMV gene expression responsible for induction of increased intracellular free [Ca$^{++}$]

| Treatment | | Fluorescence units[1,2] | % change of fluorescence | % inhibition of fluorescence change |
|---|---|---|---|---|
| Virus | Drug | | | |
| None | | 41 | | |
| CMV[3] | | 63 | +53.6 | |
| CMV + | Cycloheximide (0-6 h) | 52 | +27/9 | 42.5 |
| None | Cycloheximide[4] (0-6 h) | 36.5 | −11 | |
| CMV + | Cycloheximide (0-6 h) | 45.5 | +15.9 | 26.7 |
| + | 3'-deoxyadenosine[5] (6-24 h) | | | |
| | Cycloheximide (0-6 h) | 37.5 | −8.5 | |
| + | 3'deoxyadenosine (6-24 h) | | | |

[1]Measured at 24 h postinfection.
[2]Human embryo thyroid fibroblasts.
[3]MOI 3 PFU/ml
[4]Cycloheximide 10 ug/ml
[5]3'-deoxyadenosine (cordycepin) 20 ug/ml.

To more definitively determine the phase of CMV gene expression responsible for the increase in IF [Ca$^{++}$] more stringent conditions were used. Infected cells were treated with CH from −2 h PI through the time of virus absorption, and up to 2, 4, or 6 h PI. Then the CH was washed out and the cells were maintained through 24 h PI in the presence or absence of 3'-deoxyadenosine. Data summarized in Table 7 indicate that there was no significant difference between the Quin-2 fluorescence of CMV-infected cells in the presence or absence of 3-deoxyadenosine, indicating that the CMV-induced rise in intracellular free [Ca$^{++}$ is an immediate early function.

TABLE 7

Phase of CMV Gene Expression Responsible for Induction of Increased Intracellular Free [Ca$^{++}$]

| Treatment | | | Fluorescence units | % change in flourescence units |
|---|---|---|---|---|
| CMV[1] | Cycloheximide[2] | 3'-deoxyadenosine[3] | | |
| − | − | − | 33.5 | — |
| + | − | − | 50 | 49.3 |

TABLE 7-continued

Phase of CMV Gene Expression Responsible for Induction of Increased Intracellular Free [Ca++]

| Treatment | | | Fluorescence | % change in flourescence units |
|---|---|---|---|---|
| CMV[1] | Cycloheximide[2] | 3'-deoxyadenosine[3] | units | |
| + | −2 to 2 hr. | — | 47 | 40.3 |
| + | −2 to 2 hr. | 2 to 24 hr. | 50 | 49.3 |
| + | −2 to 4 hr. | — | 45 | 34.3 |
| + | −2 to 4 hr. | 4 to 24 hr. | 51 | 52.2 |
| − | −2 to 6 hr. | — | 29 | −13.4 |
| + | −2 to 6 hr. | — | 41 | 22.4 |
| − | −2 to 6 hr. | 6 to 24 hr. | 35 | 4.5 |
| + | −2 to 6 hr. | 6 to 24 hr. | 47 | 40.3 |
| − | −2 to 24 hr. | — | 33 | 0 |
| + | −2 to 24 hr. | — | 27 | −19.4 |
| − | — | 0–24 | 34 | 0 |

[1]MOI 3 PFU/ml.
[2]Cycloheximide 10 ug/ml.
[3]3'deoxyadenosine (cordycepin) 20 ug/ml.
[4]Measured at 24 hr. postinfection.

7. Conservation of the capacity to induce IF [Ca++] response among CMV strains

The effect of CMV laboratory strains (AD169, Davis and C-87) on IF [Ca++] was compared. The increases in fluroescence level obtained were similar among the three laboratory strains. Increases in fluorescence from 82% to 150% were observed. These results indicate that the IF [Ca++] response is not unique to strain AD-169, and that the ability of CMV to induce an increase in IF [CA++] is conserved among other CMV strains.

8. Effect of C++ influx blockers on CMV-induced IF [Ca++]

The sensitivity of the CMV-induced rise in IF [Ca++] to recognized Ca++ influx blockers (verapamil and nifedipine) was tested. Additon to verapamil (60 ug/ml) or nifedipine (60 ug/ml) at 0 h PI inhibited the CMV-induced increase in fluorescence when measured at 24 or 48 h PI. While verapamil inhibited the percent change in fluorescence by 75% and 51% at 24 and 48 h PI, respectively; nifedipine inhibited the fluorescence increase by 89% and 28%, respectively. Diltiazem (80 ug/ml), another Ca++ influx blocker, inhibited the increase in IF [Ca++] by almost 100% by 24 h PI, while nifedipine inhibited the fluorescence by 112% with the same experimental conditions.

9. Effect of papaverine on CMV-induced IR [Ca++]

Since CMV-induced cytopathology and CMV replication are Ca++ dependent, the effect of papaverine on the CMV-induced IF[Ca++] response was tested at various times PI. Papaverine inhibited the CMV-induced enhancement of IF[Ca++] as measured by Quin-2 fluorescence. The percent inhibition of fluorescence response was 24% by five hours PI and was maximal by 48 h PI approaching 100%. These data suggest the possibility that the effect of papaverine on CMV replication and CMV-induced cytopathology is through control of the IF[Ca++] response.

From the studies of the cytopathologic responses of cells to CMV infection, it was suggested that papaverine inhibited the development of NIs and cytomegaly. To determine if papaverine treatment actually caused a decrease in intracellular free [Ca++] in CMV-infected cells, the Quin-2 fluorescence in CMV-infected cells was measured in the presence or absence of 30 ug/ml of papaverine. At this papaverine dose, the Quin-2 fluorescence was inhibited at 24 and 48 h PI by 95% and 103%, respectively. The results suggest that some of the effect of papaverine on the cellular response to CMV and on virus replication could be due to an inhibition of the IF [Ca++] response.

10. Similarities between the effect of the Ca++ ionophore A23187 and CMV on human fibroblasts Since the late cellular responses to CMV infection were found to be induced by a Ca++ influx, then it is possible that other agents such as calcium ionophores might induce similar responses in SM and THY cells. Therefore, SM and THY cells wee treated with the Ca++ ionophore A23187 ($3 \times 10^{-5}$M). Enlarged cells resulted after 5 min exposure to the ionophore. The involvement of a Ca++ influx in cellular responses to CMV infection is thus consistent with this observation and the previous observations of inhibition of the late cellular responses to CMV by Ca++ influx blockers and cyclic nucleotide modulators.

C. Na+ responses to CMV infection

1. The effect of Na+ entry blockers on CMV-induced cytomegaly

It was hypothesized that an increase in intracellular sodium levels [Na+] secondary to the CMV-induced Ca++ influx would likely be followed by entry of water into the cell leading to cell enlargement. If this were the case, then Na+ entry blockers such as amiloride would be expected to inhibit enlargement. Indeed, if was found that when amiloride (300 uM) was added at 12 h PI, CMV-infected cells failed to enlarge to the same extent as untreated CMV-infected controls. In addition, nuclear inclusions were considerably decreased in size at 72 h PI.

2. The effect of CMV on the rate of $^{86}$Rb uptake via the Na+/K+ pump

Figure 4:
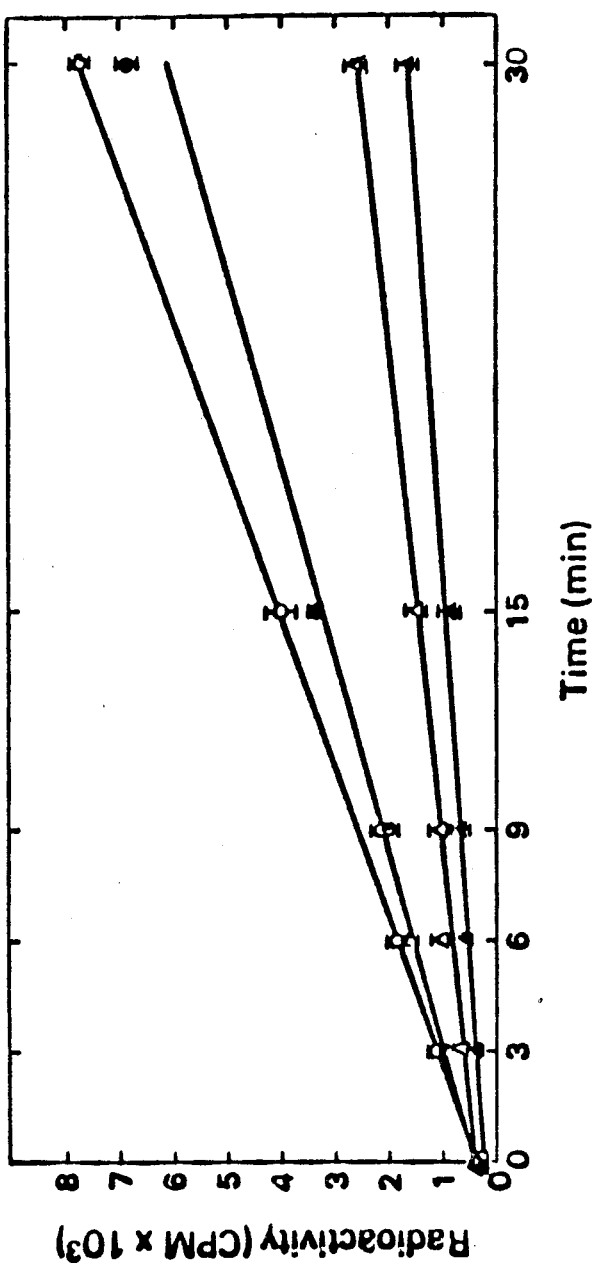
FIG. 4 illustrates the effect of CMV on the rate of $^{86}Rb$ uptake. THY cells in confluent monolayers were infected with CMV (strain AD-169) at a multiplicity of 2 PFU/cell. At 24 h PI the medium was aspirated and the cells were incubated for 0, 3, 6, 9, 15 and 30 minutes in EMEM containing 1 uCi/ml of $^{86}Rb$ and/or 120 ug/ml of Ouabain. THY cells in the absence (—o—) or presence (—△—) of Ouabain; CMV-infected THY cells in the absence (—●—) or presence of Ouabain (—▲—). Each datum point represents the mean of the determinations for 3 independent cultures processed separately, ± the standard error of the mean.

Similarly, it was hypothesized that the CMV-induced Ca++ influx is associated with or followed by a Na+ influx that would bring about the entry of water into the cell leading to cell enlargement. Since the cell volume is controlled by the ouabain-sensitive Na+/K+ pump, the activity of the pump was measured by measuring the ouabain-sensitive $^{86}$Rb uptake in CMV-infected cells in the presence and absence of ouabain. FIG. 4 shows the rate of $^{86}$Rb uptake during a 30 min interval in CMV-infected cells at 24 h PI. This experiment shows that the rate of uptake over this period is linear.

3. The effect of CMV on the ouabain-sensitive Na+/K+ ATPase

Figure 5:
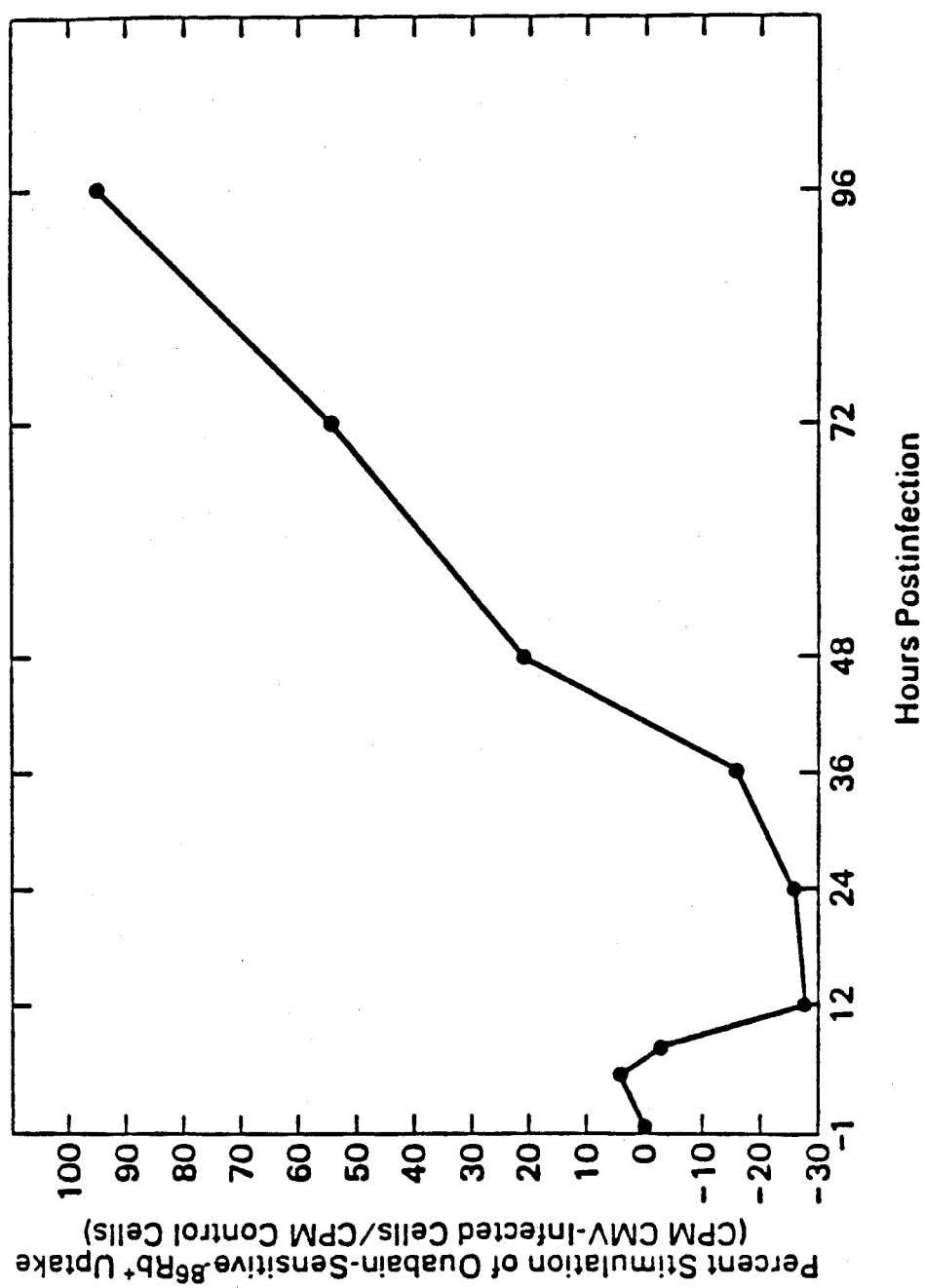
FIG. 5 shows the effect of CMV on the ouabain-sensitive $Na^+/K^+$ ATPase. THY cells in confluent monolayers were infected with CMV (strain AD-169) at a multiplicity of 3.5 PFU/cell. At selected times after infection, the medium was aspirated and the cells were incubated for 30 minutes in EMEM containing 1 uCi/ml of $^{86}Rb$ and/or 120 ug/ml of ouabain.

FIG. 5 demonstrates the effect of CMV on the activity of the Na+/K+ ATPase (pump). There is an initial phase of inhibition in the activity of the pump which is maximal by 12 to 24 h PI, which is then followed by stimulation of the activity of the pump that starts about 48 h PI and continues through 96 h PI. The enhancement of the activity of the pump coincides with the phase of cell enlargement after CMV-infection suggesting that cytomegaly might be due to increased intracellular $Na^+$ levels.

4. The effect of amiloride on CMV-induced stimulation of ouabain-sensitive $^{86}Rb$ uptake Since enhancement of the $Na^+/K^+$ pump activity is associated with increased intracellular $Na^+$, the effect of amiloride, a $Na^+$ entry blocker, was tested on the CMV-induced stimulation phase of the pump. Amiloride (200 uM) was added to CMV-infected cells at 24 h PI and the ouabain-sensitive $^{86}Rb$ uptake was measured at 48 h PI. The apparent stimulation of the CMV-induced $^{86}Rb$ uptake was inhibited by more than 77.6% to level less than that observed in the control uninfected cells during this 24 h period in the presence of amiloride. These data indicate that the CMV-induced stimulation of the pump was $Na^+$ dependent.

5. The effect of nifedipine on the ouabain-sensitive $Na^+/K^+$ pump

To determine if the enhancement of the activity of the $Na^+/K^+$ pump in CMV-infected cells was $Ca^{++}$ dependent, the effect of nifedipine on the ouabain-sensitive $^{86}Rb$ uptake was measured. Data indicated that nifedipine (30 ug/ml), when added at 0 h, inhibited the activity of the $Na^+/K^+$ pump in CMV-infected cells. In the initial phase of CMV-induced inhibition, the activity of the pump was further depressed from $-21\%$ and $-18\%$ at 12 h PI to $-67\%$ and $-83\%$ relative to the cell control, respectively.

During the CMV-induced enhancement phase, the activity of the pump was inhibited from 37.5% and 37% at 48 and 72 h PI to $-39\%$ and $-82\%$ relative to the cell control, respectively. These data suggest that the effect of CMV on the activity of the $Na^+/K^+$ pump may be regulated by the intracellular $Ca^{++}$ levels.

6. The effect of $Ca^{++}$ ionophores on the activity of the $Na^+/K^+$ pump

Since CMV has an initial phase of inhibition of the $Na^+/K^+$ pump, it was determined whether this effect was possibly $Ca^{++}$ mediated. In this experiment, two $Ca^{++}$ ionophores were used to test their effect on the ouabain-sensitive $^{86}Rb$ uptake in the uninfected cells. Table 8 shows that both $Ca^{++}$ ionophores (A21387, Ionomycin) at a concentration of $1 \times 10^{-5}M$ were able to inhibit the ouabain-sensitive counts by 50%.

TABLE 6

| The effect of $Ca^{++}$ Ionophores on Ouabain-Sensitive $^{86}Rb$ Uptake | | | |
|---|---|---|---|
| | Sample | CMP[1] | % change |
| Exp. 1 | SM Cells | 6412 | |
| | SM Cells + Ionomycin[2] | 3231 | −49.6 |
| Exp. 2 | SM Cells | 5998 | |
| | SM Cells + A23187[2] | 2973 | −50.4 |

Figure 6:
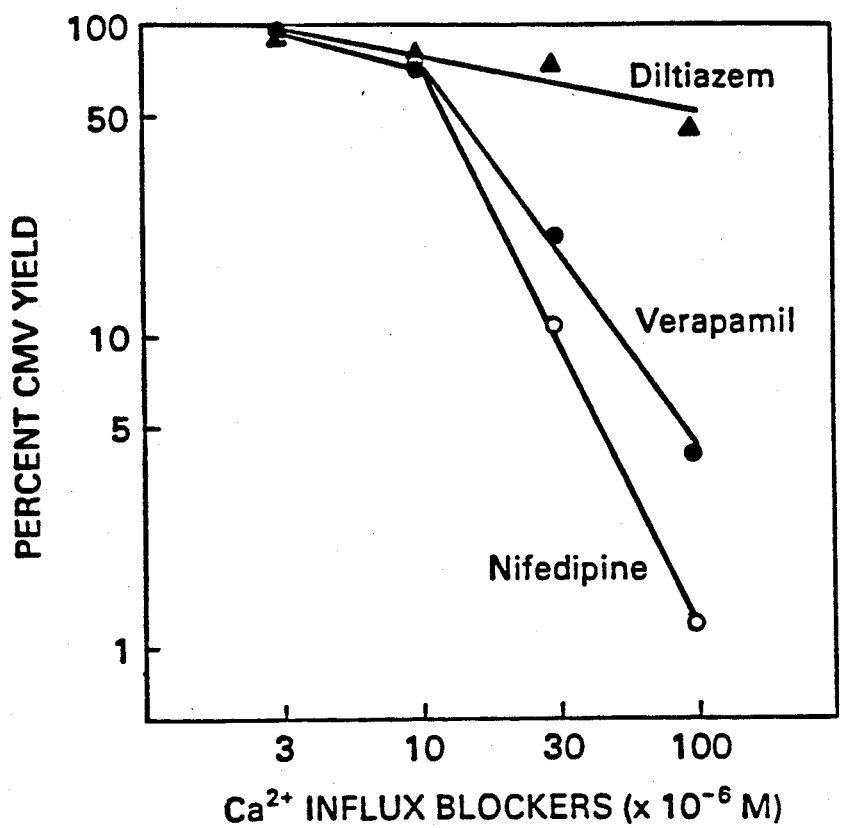
FIG. 6 demonstrates the inhibition of CMV replication by $Ca^{++}$ influx blockers. Human embryo skin muscle (SM) cells were infected with CMV (strain AD-169, MOI=5 PFU/cell) and treated at 0 h PI with several concentrations of diltiazem (▲), verapamil (●) or nifedipine (o). Virus yields were measured at 96 h PI by plaque assay.

[1]Thirty min. pulse-label from 120 to 150 min. after addition of the ionophores.
[2]$1 \times 10^{-5}M$ D. Inhibition of CMV and herpes simplex virus replication 1. By $Ca^{++}$-influx blockers $Ca^{++}$ influx blockers have been divided into 3 classes based on differing tissue specificities. Verapamil, nifedipine and diltiazem are the most extensively studied prototypes of the three classes of $Ca^{++}$ influx blockers. FIG. 6 summarizes the results obtained when the effect of a representative of each of the three classes of $Ca^{++}$ influx blockers was studied on the replication of CMV in SM cells. Nifedipine was the most effective of the three $Ca^{++}$-influx blocking drugs, while diltiazem was not effective in inhibiting CMV yields. Inhibition of CMV yields was greater than 95% at a concentration with $10^{-4}M$ of either nifedipine or verapamil. Approximately $2 \times 10^{-5}M$ nifedipine or verapamil was needed to obtain 50% inhibition of CMV yield.

Figure 7:
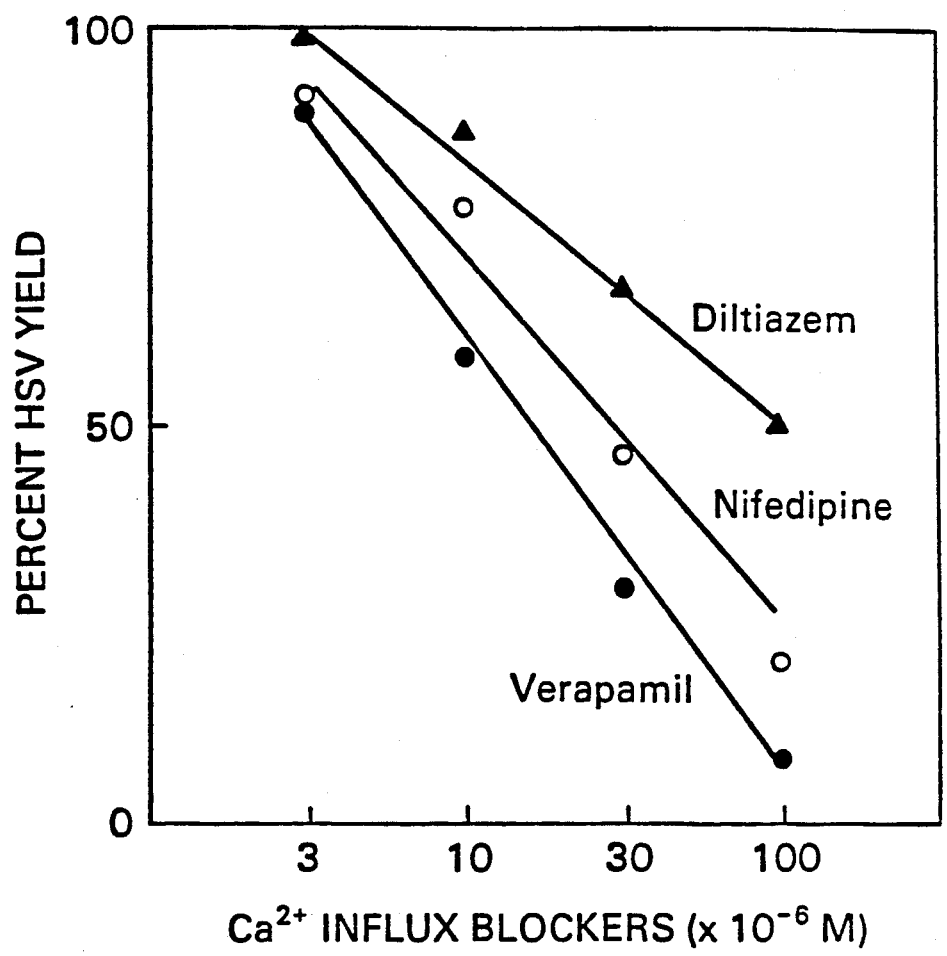
FIG. 7 demonstrates the inhibition of HSV-1 replication by $Ca^{++}$ influx blockers. SM cells were infected with HSV-1 (strain KOS, MOI=3 to 5 PFU/cell). Virus yields were measured at 30-36 h PI by plaque assay. Cells were treated at 0 h PI. (●), verapamil; (o), nifedipine; (▲), diltiazem. Data plotted are the average of 2 or more experiments.

HSV-1 replication was somewhat less sensitive to the antiviral effect of $Ca^{++}$ influx blockers than CMV replication (FIG. 7). A dose of $10^{-4}$ verapamil inhibited HSV-1 yields by 90%. The same dose of nifedipine resulted in 77.2% inhibition of the HSV-1 yield. Examination of FIG. 7 indicates that 50% inhibition of HSV-1 yields was obtained with a dose of approximately $3 \times 10^{-5}M$ ($1.7 \times 10^{-5}$ g/ml) nifedipine or $1.6 \times 10^{-5}M$ ($7.8 \times 10^{-6}$ g/ml) verapamil. A concentration greater than $10^{-4}M$ ($4.5 \times 10^{-5}$ g/ml) of diltiazem was required to obtain 50% inhibition of HSV-1 yields.

As a first step in increasing our understanding of the mechanism of antiviral activity of $Ca^{++}$ influx blockers, a kinetic study was done in cells infected with HSV-1 and treated with verapamil. Confluent SM cells were pretreated with 30 ug/ml of verapamil at various times before virus infection. Virus yields were measured at 33 h PI. Results are shown in Table 9. Pretreatment of cells with verapamil at 24, 12 or 2 h before virus infection resulted in no significant inhibition of HSV-1 yields (7–40%). Pretreatment of cells with verapamil and posttreatment after virus infection resulted in levels of inhibition of HSV-1 yields similar to post-treatment with verapamil alone. Enhanced inhibition was not observed following pretreatment. These data suggest that the inhibitory effect of verapamil against HSV-1 replication begins only after virus infection of cells. Establishment of an antiviral state as observed with interferon treatment seems to be unlikely with verapamil and efficient replication of HSV-1 apparently requires a $Ca^{++}$ influx.

TABLE 9

| Effect of Pretreatment with Verapamil on the Replication of HSV-1 | | | |
|---|---|---|---|
| Type of treatment | Duration of treatment | Percent inhibition[b] of HSV yield | Fold inhibition[c] |
| Pretreatment alone | −12 to −1 h | 3 | 1.03 |
| | −3 to −1 h | 39 | 1.67 |
| Pre- and post treatment | −12 to −1, 0 to 33 h | 89 | 9.06 |
| | −3 to −1, 0 to 33 h | 90 | 10 |
| Posttreatment | 0 to 33 h | 92 | 12.5 |

[a]SM cells were pretreated with 30 ug/ml of verapamil at various times before virus infection. HSV-1 (strain KOS) was applied to the cells at an MOI of 6.3 PFU/cell. Virus yields were measured at 33 h PI.
[b]Calculated relative to untreated control virus yields.
[c]Fold inhibition = $\frac{100}{100 - \% \text{ inhibition}}$ 2. The effect of increased extracellular $[Ca^{++}]$ on the antiviral effects of $Ca^{++}$ influx blockers HSV-1 and CMV replication are sensitive to the effect of $Ca^{++}$ influx blockers. In other words, the replication of HSV-1 and CMV may induce the rapid influx of $Ca^{++}$ into the cell from the extracellular medium. Based on this observation, it was reasoned that the antiviral effect of $Ca^{++}$ influx blockers would be decreased by increasing the concentration of extracellular $Ca^{++}$. This possibility was tested using Eagle's minimal essential medium (EMEM) with varying concentrations of Ca$^{++}$ as CaCl$_2$, 1.8 mM, 3.6 mM, and 7.2 mM. Four drugs from three classes of Ca$^{++}$ influx blockers were tested in the presence of increased extracellular [Ca$^{++}$]. Verapamil (30 ug/ml) inhibited HSV-1 yields by 99%. The inhibitory effect of verapamil was decreased by increasing extracellular [Ca$^{++}$]. More than a 2-fold increase in HSV-1 yield was observed with 3.6 mM Ca$^{++}$ and almost 4.8-fold more virus was obtained with 7.2 mM Ca$^{++}$. The results with nifedipine were similar. 38% and 46% greater virus yields with increasing extracellular [Ca$^{++}$] of 3.6 and 7.2 mM, respectively. The antiviral effect of gallopamil, a derivative of verapamil, was also decreased with 3.6 mM or 7.2 mM Ca$^{++}$. Virus yields were increased by 82% in 3.6 mM or 7.23 mM Ca$^{++}$. Virus yields were increased by 82% in 3.6 mM Ca$^{++}$ and by 50% in 7.2 mM Ca$^{++}$. The yields of HSV from cells treated with diltiazem were not greatly affected by altering the extracellular [Ca$^{++}$] concentration. Less than a 10% increase in virus yield was observed in the presence of diltiazem with 3.6 mM or 7.2 mM Ca$^{++}$. These data support the hypothesis that the antiviral effect of Ca$^{++}$ influx blockers is related to their ability to block the influx of extracellular Ca$^{++}$.

In addition to the recognized Ca$^{++}$ influx blockers, one cyclic nucleotide modulator was tested. Since papaverine has been postulated also to affect Ca$^{++}$ fluxes, the effect of increased extracellular [Ca$^{++}$] on papaverine inhibition of HSV yields was examined. Papaverine (30 ug/ml) inhibited HSV-1 yield by about 85% in the presence of 1.8 mM Ca$^{++}$. By increasing the extracellular calcium concentration, HSV-1 yields were increased by 101% (3.6 mM Ca$^{++}$) or 136% (7.2 mM Ca$^{++}$).

3. By cyclic nucleotide modulators

Figure 8:
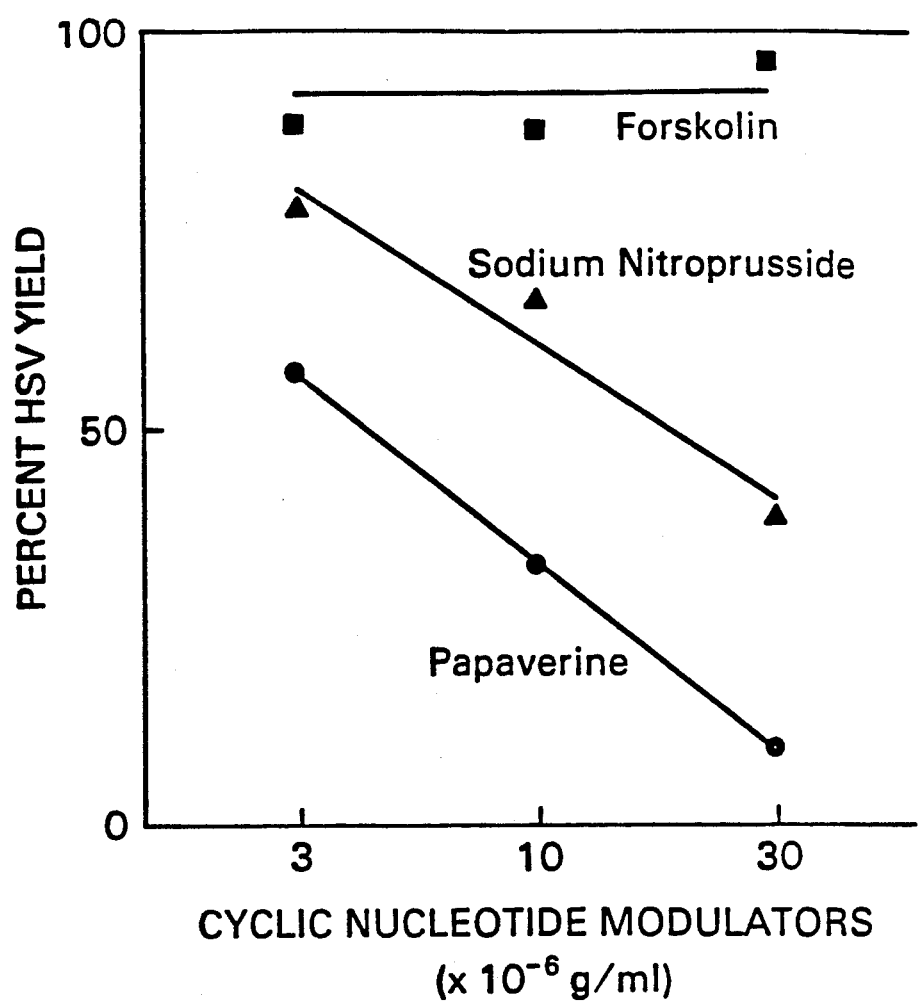
FIG. 8 demonstrates the inhibition of HSV-1 replication by cyclic nucleotide modulators. SM cells were infected with HSV-1 (strain KOS, MOI=3 to 5 PFU/cell). Virus yields were measured at 30-36 h PI by plaque assay. Cells were treated at 0 h PI. (●), papaverine; (▲), sodium nitroprusside; (■), forskolin. Data plotted are the average of 2 or more experiments.
Figure 9:
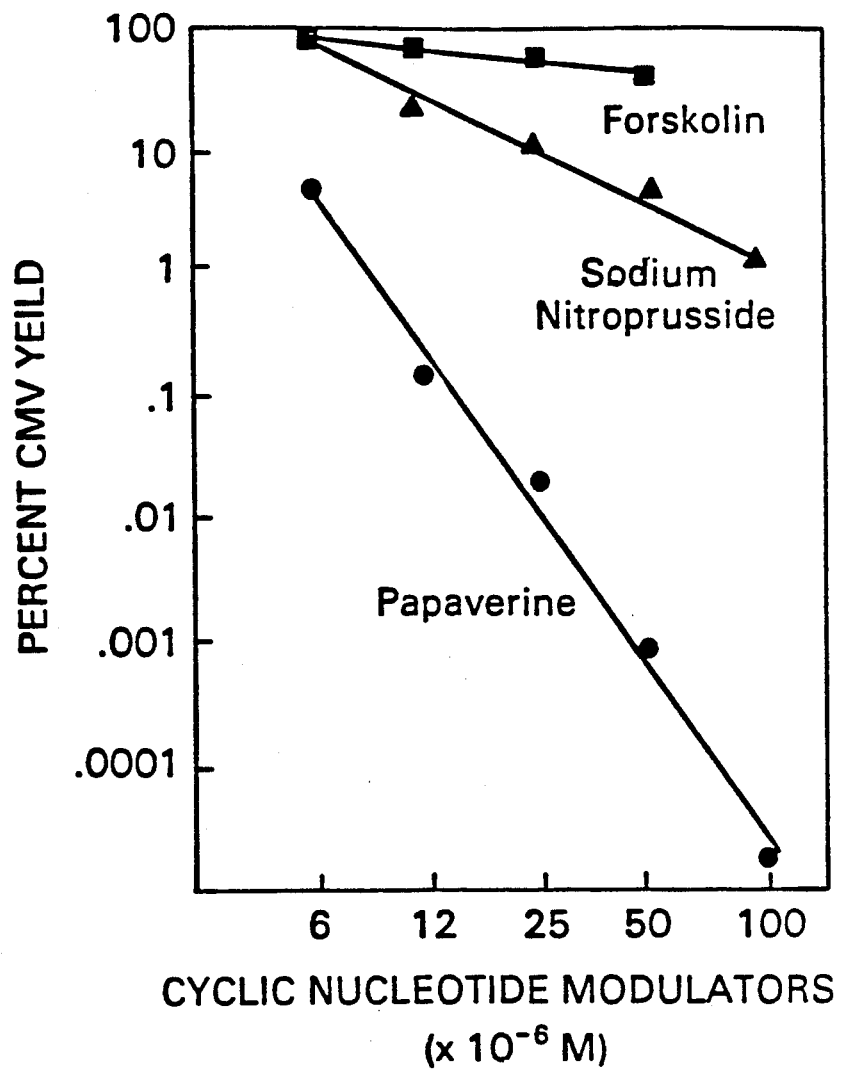
FIG. 9 demonstrates the inhibition of CMV replication by cyclic nucleotide modulators. Human embryo skin muscle (SM) cells were infected with CMV (strain AD-169, MOI=3 to 5 PFU/cell) and treated at 0 h PI with various doses of cyclic nucleotide modulators. Virus yields were measured at 96 h PI by plaque assay. (●), papaverine; (▲), sodim nitroprusside; (■), forskolin. Data plotted are the average 3 or more experiments.

The cyclic nucleotides cAMP and cGMP have been shown to act as secondary and/or synarchic messengers and to affect Ca$^{++}$-mediated events. Thus, the effects of several drugs that increase intracellular concentrations of cAMP or cGMP or both were tested for antiviral activity. FIGS. 8 and 9 summarize the results of experiments with HSV-1- and CMV-infected cells. Papaverine increases the intracellular levels of both cyclic nucleotides by inhibiting the phosphodiesterase activities. Papaverine inhibited HSV-1 replication in a dose-dependent manner (FIG. 8). A dose of 30 ug/ml of papaverine inhibited HSV-1 replication by about 90%. A dose of 10 ug/ml of papaverine resulted in 70% inhibition while a dose of 3 ug/ml of papaverine exerted less than a 50% inhibition of HSV yields. Nitroprusside increases the intracellular level of cGMP, but not of cAMP. Nitroprusside treatment was not as effective as papaverine. Forskolin, which increases the level of cAMP, did not have an inhibitory effect on HSV-1 replication. These results, when considered together with those for papaverine and nitroprusside, suggest that the increase of both cyclic nucleotides may effect the replication of HSV-1, but that increases in the level of either cGMP or cAMP alone may not be as important as direct effects on Ca$^{++}$ influx or the coordinate increases of both cyclic nucleotides.

While cyclic nucleotide modulators gave no better inhibition of HSV-1 replication than Ca$^{++}$ influx blockers, papaverine showed a dramatic inhibition if CMV replication (FIG. 9). More than 99.9999% ($10^6$-fold) inhibition of CMV yield was observed with $10^{-4}$M ($3.4 \times 10^{-5}$ g/ml) papaverine. 99% (100-fold) inhibition of CMV yield was obtained at less than $10^{-5}$M of papaverine. Sodium nitroprusside at $10^{-4}$M ($2.6 \times 10^{-5}$ g/ml) resulted in about 99% inhibition of CMV yield. Forskolin, as in the case of HSV-1 infection, was not effective against CMV infection. The drop in virus yield at a concentration of $10^{-4}$M forskolin might be due to the toxicity of forskolin at the time of this particular experiment, but was not a consistent finding. A comparison of data from FIGS. 8 and 9 suggest that CMV replication is more sensitive than HSV-1 replication to the increase of both cyclic nucleotides or cGMP alone.

4. Comparison of the anti-CMV effect of two papaverine preparations

To ensure that the effect of papaverine (Eli Lilly, Indianapolis, IN) was due to papaverine and not due to other elements in papaverine preparations as supplied by Lilly for injection, the anti-CMV effect of two papaverine preparations (papaverine in solution from Eli Lilly, papaverine in solid form from Sigma) was compared. Both preparations of papaverine were found to be similarly effective against CMV replication. Apparently the antiviral effect of Lilly's papaverine preparation is due to papaverine.

5. The antiviral effect of combination treatment with papaverine and Ca$^{++}$ influx blockers Combination antimicrobial therapy has proved to be effective in curing several bacterial diseases. Moreover, combination treatment permits the reduction of the dosage of antibiotics to lessen toxicity and to prevent the appearance of antibiotic-resistant strains. With these advantages in mind, combination treatment with papaverine and Ca$^{++}$ influx blockers was tried. Suboptimal doses of each drug were used. The results (Table 10) suggest the possibility of synergistic effects with combination treatment of a cyclic nucleotide modulator (e.g.,-- papaverine) and a calcium influx blocker (e.g.---verapamil or nifedipine). Verapamil (30 u M ) resulted in a 10-fold inhibition and papaverine (5 u M) resulted in 18-fold inhibition of CMV yields. When both verapamil (30 u M) and papaverine (5 u M) were used in combination, 112-fold inhibition of CMV yields was obtained. A somewhat greater synergistic effect was observed with the combination of 30 u M nifedipine and 5 u M papaverine. Diltiazem, however, did not demonstrate synergistic effects when used in combination with papaverine. In fact, less inhibitory effect was evident with combination treatment with diltiazem and papaverine than papaverine alone. These results, in part, correlate with the observation that verapamil and nifedipine were more effective in inhibiting CMV replication than diltiazem.

TABLE 10

Combination Treatment with Papaverin and Ca$^{++}$ Influx Blockers

| Ca$^{++}$ influx blocker | No papaverine | | With papaverine | |
|---|---|---|---|---|
| | CMV yield | Fold Inhibition | CMV yield | Fold Inhibition |
| None | 3.5 × 10$^7$ | | 2.0 × 10$^6$ | 18 |
| Verapamil | 3.5 × 10$^6$ | 10 | 3.1 × 10$^5$ | 112 |
| Nifedipine | 7.5 × 10$^6$ | 4.8 | 2.2 × 10$^5$ | 159 |
| Diltiazem | 1.2 × 10$^7$ | 3.0 | 9.7 × 10$^6$ | 3.6 |

Human embryonic skin muscle (SM) cells were infected with CMV (strain AD169, MOI = 3.0 PFU/cell). After 1 h adsorption at 37° C., the Ca$^{++}$ influx blockers were added to infected cultures to 30 uM in the presence or absence of 5 uM papaverine. Media were changed at 48 h with fresh drugs. Virus yields were determined at 96 h PI.

7. The relationship between the time of removal of papaverine and inhibition of CMV yields As shown in Table 11, the antiviral action of papaverine is readily reversible through at least 6 h PI. The drug is apparently effectively washed out since yields from cells washed at 4 and 6 h were enhanced over untreated controls. Even when the drug was washed out at later times through 72 h PI, yields from 37% to 14% of the control were obtained. Thus, the inhibitory effect of papaverine is reversible. The diminishing yields obtained following reversal of the papaverine block suggest that at later times the inhibitory action of papaverine may not be reversible even though the drug has been effectively removed. This possibility will be tested in future studies. Furthermore, it is not clear from this experiment what is the fate of the papaverine-treated, CMV-infected cell. This question will also be answered in future studies.

TABLE 11

Effect of the Time of Removal of Papaverine on its Inhibitory Effect of CMV Replication

| Time of removal (h PI) | CMV Yields (PFU/ml) No papaverine | Papaverine | Percent of control[b] |
|---|---|---|---|
| None | $2.3 \times 10^6$ | $7.8 \times 10^2$ | 0.034 |
| 2 | $3.3 \times 10^6$ | $2.1 \times 10^6$ | 64 |
| 4 | $3.1 \times 10^6$ | $5.3 \times 10^6$ | 171 |
| 6 | $2.7 \times 10^6$ | $4.5 \times 10^6$ | 167 |
| 12 | $1.0 \times 10^7$ | $3.7 \times 10^6$ | 37 |
| 24 | $2.2 \times 10^7$ | $5.8 \times 10^6$ | 26 |
| 48 | $1.5 \times 10^7$ | $3.9 \times 10^6$ | 26 |
| 72 | $1.7 \times 10^7$ | $2.4 \times 10^6$ | 14 |

[a]SM cells were infected with CMV (strain AD169) at a MOI of 3.6 PFU/cell. Half of the infected cultures were treated with EMEM containing 10 ug/ml papaverine at 0 h PI. At various times after infection, cells were washed three times and fed with fresh EMEM. CMV yields were determined at 96 h PI, except for the 72 h PI wash which was harvested at 120 h PI.
[b]Relative to untreated cultures that were washed at same time as papavine-treated cultures.

E. Stage od CMV replication sensitive to the antiviral effects of papaverine

1. Time of addition studies

As papaverine was highly effective in inhibiting CMV replication, the time point at which the replication of CMV is sensitive to treatment with papaverine was determined. Cells were infected with CMV and treated with 10 ug/ml of papaverine at various times before or after virus infection. Pretreatment with papaverine at 24, 12 or 2 h before virus infection resulted in no inhibition of the CMV yields, nor the enhancement of antiviral activity when followed by post-treatment at 0 h PI. Addition of papaverine at early times after virus infection through 6 h PI gave virtually identical inhibitory effects on CMV replication. With the addition of drug after 6 h, the effect of papaverine dropped approximately 5- to 10-fold with each successive 12 to 24 h delay; however, the addition of papaverine as late as 48 h PI resulted in a significant inhibition of CMV yields.

2. Viral DNA synthesis a. HSV-1 DNA synthesis

The time of addition studies suggested this antiviral effect was most pronounced when papaverine was added before the time of initiation of CMV DNA synthesis. The possibility that smooth muscle-relaxing agents were inhibiting viral DNA synthesis was first examined by testing the effect of $Ca^{++}$ influx blockers or papaverine on the synthesis of DNA in cells infected with HSV-1. The experiments were designed so that total radioactivity from infected cells was representative of the rate of HSV-1 DNA synthesis because at the time of radioactive labelling cellular DNA synthesis is almost completely shut down. A representative drug from each of the three classes of $Ca^{++}$ influx blockers was tested for its ability to inhibit DNA synthesis in SM cells infected with HSV-1 strain KOS. Treatment of infected cells with verapamil or nifedipine at 30 ug/ml inhibited the incorporation of radioactive thymidine by 51–60%. Diltiazem was not inhibitory. $Ca^{++}$ influx blockers, however, inhibited the incorporation of $^3H$-thymidine in mock-infected cells more efficiently than in HSV-1 infected cells. The results with papaverine were similar to those observed with $Ca^{++}$ influx blockers except that both mock-infected cells had similar levels of inhibition of DNA synthesis.

b. CMV DNA synthesis

In CMV-infected cells, cellular DNA synthesis is stimulated in the early phase of virus infection, but during the late phase nearly all DNA synthesized is of virus origin. Thus, measurement of $^3H$-thymidine incorporated during the late phase of CMV infection represents CMV-specific DNA synthesis. Treatment of CMV-infected cells with $Ca^{++}$ influx blockers resulted in a substantial decrease in the rate of CMV DNA synthesis. Again, more efficient inhibition of DNA synthesis occurred in mock-infected cells than in virus-infected cells. The level of inhibition of DNA synthesis of CMV-infected cells was lower than the level of inhibition of CMV yield.

Papaverine is the most potent of the smooth muscle-relaxing agents which inhibit the replication of CMV. More than 100,000-fold inhibition of CMV replication usually is observed with 30 ug/ml of papaverine. When the effect of papaverine on the synthesis of DNA in cells infected with CMV was tested, however, only a 91% or 11-fold inhibition of DNA synthesis was observed. Apparently this reduction in the rate of incorporation of $^3H$-thymidine represented inhibition of DNA synthesis rather than a delay. When a time-course study done with 10 ug/ml of papaverine, no displacement of the pattern of CMV DNA synthesis was observed; in contrast, the extent of inhibition increased with elapsed time after infection and papaverine treatment as illustrated by Table 12.

TABLE 12

Effect of Papaverine on the synthesis of DNA in SM Cells Infected with CMV: A Kinetic Study

| Labeling period (h PI) | CPM No papaverine | Papaverine | Percent inhibition |
|---|---|---|---|
| 0–24 | 9315 | 6302 | 32 |
| 24–48 | 26864 | 8142 | 70 |
| 48–72 | 108636 | 22216 | 80 |
| 72–96 | 87508 | 7786 | 91 |
| 96–120 | 57116 | 2876 | 95 |

Human embryo skin muscle (SM) cells were grown on 35 mm dishes and infected with CMV (strain Ad-169) at a MOI of 3.4 PFU/ml. Papaverine was added at 0 h PI to make an initial concentration of 10 ug/ml. Medium was changed at 48 h PI with fresh papaverine. Concentrated $^3H$—thymidine (specific activity = 20 Ci/mmol) was added at the times indicated after CMV infection to a final concentration of 10 uCi/ml.

The disparity between the levels of inhibition achieved by papaverine of virus yield and virus DNA synthesis suggested that inhibition of CMV resulted from mechanisms which affected replication steps other than just DNA synthesis, or that the papaverine was not being applied at the optimal time. A time of addition study was designed and done at a MOI of 3.4 PFU/cell. Pretreatment of cells with papaverine had no effect on CMV DNA synthesis. Treatment of cells with papaverine at any time from 0 to 24 h PI resulted in a similar level of inhibition of DNA synthesis: about 90% to 95%.

Figure 10:
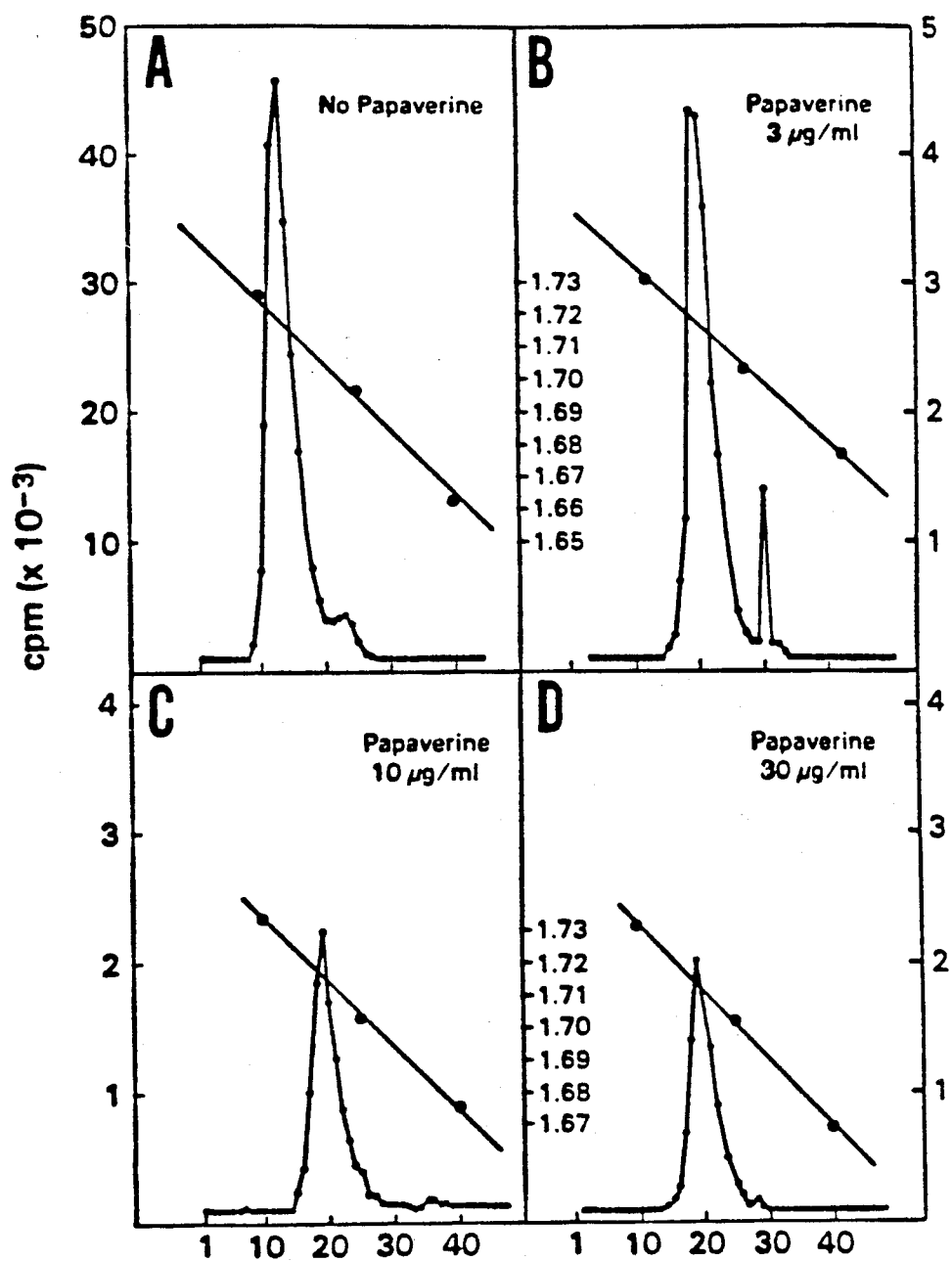
FIG. 10 demonstrates the isopyinic centrifugation of DNA isolated from CMV-infected cells. Human embryo skin muscle (SM) cells were infected with CMV (strain AD-169, MOI=3 PFU/cell) and treated with various concentrations of papaverine at 0 h PI. Cells were labelled with $^3H$-thymidine (10 uCi/ml) from 72 to 96 h PI. (A) No papaverine; (B) papaverine 3 ug/ml; (C) papaverine 10 ug/ml; (D) papaverine 30 ug/ml.

In spite of numerous experiments which were performed on CMV DNA synthesis, it was possible that cellular DNA synthesis was making a much larger contribution to the overall rate of $^3$H-thymidine incorporation than predicted. To determine if the radioactivity measured in CMV-infected cells was truly representative of CMV DNA synthesis, viral and cellular DNA were separated using CsCl density gradient centrifugation. FIG. 10 shows the radio-activity measured in each fraction collected from the bottom of representative gradients. At 72-96 h PI, almost no cellular DNA was found; most of the radioactivity was found in a peak with the recognized density (1.716 g/cm$^3$) of CMV DNA. Since from 72 to 96 h PI, CMV DNA synthesis reaches the maximum rate at this relatively high MOI, it is unlikely that cellular DNA synthesis contributed sufficiently to the overall rate of $^3$H-thymidine incorporation to result in the erroneous interpretation of the earlier data.

F. Structure-activity relationships of papaverine-related compounds

Figure 11:
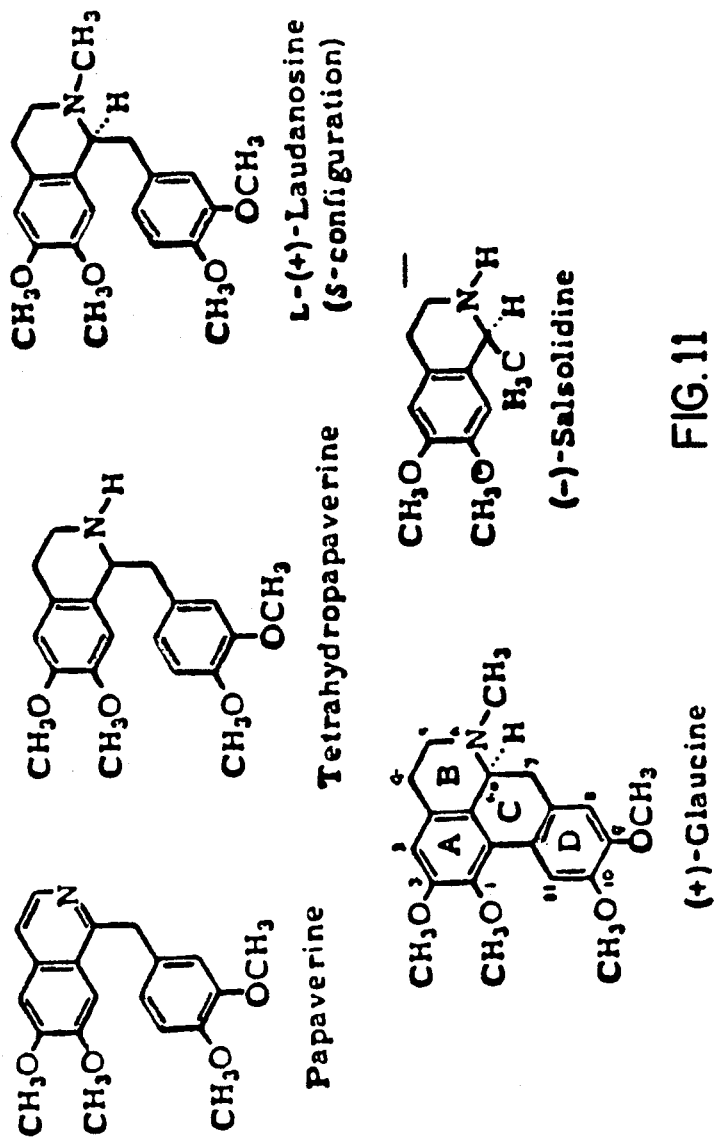
FIG. 11 illustrates the structure of isoquinolines and other chemicals related to papaverine.

Since papaverine has proven to be the most potent anti-CMV drug tested in our protocols thus far, studies of the structural specificity of the antiviral action of papaverine were initiated by comparing the antiviral activities of several compounds which are structurally related to papaverine and commercially available. Glaucine, laudanosine, salsolidine and tetrahydropapaverine were tested. Their structures, as well as the structure of papaverine, are shown in FIG. 11. All these drugs were dissolved in 70% ethanol to make stock solutions with an initial concentration of 40 mg/ml. Subsequent dilutions were mode with water to make working solutions of 10 mg/ml.

Results of virus yield assays in the presence or absence of drugs from this group of isoquinolines are shown in Table 13. No significant inhibition of CMV replication was observed with these drugs. Only tetrahydropapaverine at the highest concentration resulted in more than 10-fold inhibition of CMV replication. Controls consisting of ethanol at a concentration corresponding to that contained in the highest concentration of the drugs tested were examined for antiviral effects and 3- to 4-fold inhibition of CMV replication was observed.

Therefore, tentatively, recognizing that this is a single experiment, it appears that the nitrogen on the isoquinoline ring with an electron available for covalent bond formation is critical to the antiviral activity of papaverine. When hydrogen occupies this site (tetrahydropapaverine), then the inhibitory activity is reduced from 99,99982% inhibition to 89% inhibition at equimolar doses of 100 u M. When a methyl group occupies this site (laudanosine), the antiviral activity is lost almost entirely. The results with salsolidine and glaucine add further support to this view. It will be appreciated that those papaverine family agents not found to have appreciable antiviral activity do not have a true isoquinoline ring in that the aromaticity of the ring is lost upon addition of substituents to the ring nitrogen. Moreover, an additional papaverine family agent which has shown good antiviral activity, ethaverine, does have an isoquinoline ring (ethaverine has the same chemical structure as papaverine except with ethoxy groups in place of the four methoxy groups of papaverine). Therefore, the present invention is directed in particular to papaverine family agents having the aromatic isoquinoline ring.

TABLE 13

Effect of Papaverine-Related Compounds on the Replication of CMV

| Drugs[a] | Dose (uM) | CMV Yields (PFU/ml)[b] | Percent of Control |
|---|---|---|---|
| None | | $1.8 \times 10^7$ | 100 |
| Laudanosine | 3 | $2.0 \times 10^7$ | 111 |
| | 10 | $1.0 \times 10^7$ | 56 |
| | 30 | $2.4 \times 10^7$ | 133 |
| | 100 | $1.3 \times 10^7$ | 72 |
| Glaucine | 3 | $2.1 \times 10^7$ | 117 |
| | 10 | $1.1 \times 10^7$ | 61 |
| | 30 | $2.1 \times 10^7$ | 117 |
| | 100 | $1.6 \times 10^7$ | 89 |
| Salsolidipine | 3 | $1.3 \times 10^7$ | 72 |
| | 10 | $1.4 \times 10^7$ | 78 |
| | 30 | $1.4 \times 10^7$ | 78 |
| | 100 | $4.4 \times 10^6$ | 24 |
| Tetrahydro-papaverine | 3 | $1.5 \times 10^7$ | 83 |
| | 10 | $1.7 \times 10^7$ | 94 |
| | 30 | $4.8 \times 10^6$ | 27 |
| | 100 | $1.9 \times 10^6$ | 11 |

[a]Drugs were dissolved in 70% ethanol to make an initial concentration of 40 mM and subsequently diluted with water to 10 mM. Further dilutions were made with EMEM to make 100, 30, 10 and 3 uM.
[b]SM cells and CMV strain AD169 at a MOI of 3.7 PFU/cell were used. Medium was changed at 48 h PI and virus yields were determined at 96 h PI.

G. Inhibition of CMV and HSV-1 Replication by Combined Treatment with Interferon and Ca++ Influx blockers.

In addition to demonstrating synergistic action when administered to infected cells in combination with each other, the pharmacologic agents disclosed by the present invention exhibit a synergistic antiviral when administered in combination with alpha interferon (IFN alpha). This was demonstrated by treating infected cells with a combination which included IFN alpha and verapamil. THY cells were treated with 1000 U/ml of recombinant type IFN alpha (obtained from Schering, Kenilworth, N.J.) 24 h before CMV infection. After CMV infection the cells were treated with 1000 U/ml of IFN alpha and/or 15 ug/ml of verapamil. Media were changed at 48 h PI. Virus yields were measured at 96 h PI. As seen in Table 14, CMV replication was inhibited by 1.9-fold with 15 ug/ml of verapamil and by 3.6-fold with 1000 U/ml of IFN alpha. Combined treatment with verapamil and IFN alpha gave a 26.3-fold inhibition of CMV yield. This number is almost 5-fold higher than 5.5 which is the sum of the levels of inhibition of the two drugs alone (3.6 and 1.9).

TABLE 14

| | Inhibition of CMV replication by IFN alpha and verapamil | | |
|---|---|---|---|
| Treatment | Virus yield[a] (pfu/ml) | Percent Inhibition | Fold Inhibition |
| None | $4.78 \times 10^6$ | | |
| IFN a[b] | $1.34 \times 10^6$ | 72.0 | 3.6 |
| Verapamil[c] | $2.50 \times 10^6$ | 47.7 | 1.9 |
| IFN a + verapamil[d] | $1.83 \times 10^5$ | 96.2 | 26.3 |

[a]THY cells were infected with CMV (strain AD169, MOI = 4.5 pfu/cell). Media were changed at 48 PI. Virus yields were measured at 96 h PI.
[b]1,000 U/ml of recombinant IFN alpha was used.
[c]15 ug/ml.

This apparent synergistic effect was also observed when cells were pretreated with IFN alpha, infected with HSV-1, and post-treated with the combination of IFN alpha and verapamil (Table 15). 2000 U/ml of IFN alpha alone gave 33-fold inhibition of HSV-1 yields and 30 ug/ml of verapamil resulted in 33-fold inhibition. Combined treatment of 2000 U/ml of IFN alpha and 30 ug/ml of verapamil gave a 500-fold inhibition of HSV-1 yield.

TABLE 15
Inhibition of HSV-1 Replication of IFN alpha and Verapamil

| Treatment | Virus yield[a] (pfu/ml) | Percent Inhibition | Fold Inhibition |
|---|---|---|---|
| None | $1.2 \times 10^7$ | | |
| IFN a[b] | $3.5 \times 10^5$ | 97 | 33 |
| Verapamil[c] | $3.5 \times 10^5$ | 97 | 33 |
| IFN a + verapamil[d] | $2.5 \times 10^4$ | 99.8 | 500 |

[a]SM cells were infected with HSV-1 (strain KOS, MOI = 5 pfu/cell). Virus yields were measured at 24 h PI.
[b]2,000 U/ml of recombinant IFN alpha was used.
[c]30 ug/ml.
[d]2,000 U/ml of IFN alpha + 30 ug/ml of verapamil.

A more detailed study with IFN alpha and verapamil in HSV-1 infected human cells (Table 16) suggests that the synergistic effect may be optimized when relatively high (more than 333 U/ml) doses of IFN alpha was used in combination with verapamil doses as low as 3.7 u g/ml. A high concentration of verapamil (33 u g/ml) and lower dose of IFN alpha (111 U/ml) resulted in little synergistic effect.

TABLE 16
Inhibition of HSV-1 Replication by Combined Treatment of IFN alpha and Verapamil

| IFNa (U/ml)[b] | Verapamil (ug/ml) | | | |
|---|---|---|---|---|
| | 0 | 3.7 | 11 | 33 |
| 0 | $1.03 \times 10^8$ (1) | $6.25 \times 10^7$ (1.6) | $8.25 \times 10^7$ (1.25) | $1.45 \times 10^7$ (7.1) |
| 111 | $3.25 \times 10^7$ (3.2) | $3.25 \times 10^7$ (3.2) | $1.83 \times 10^7$ (5.6) | $1.05 \times 10^7$ (9.8) |
| 333 | $2.63 \times 10^7$ (3.9) | $1.10 \times 10^7$ (9.4) | $1.08 \times 10^7$ (9.5) | $1.65 \times 10^6$ (62.4) |
| 1,000 | $8.75 \times 10^6$ (11.8) | $4.25 \times 10^6$ (24.2) | $4.25 \times 10^6$ (24.2) | $1.68 \times 10^6$ (61.3) |

[a]SM cells were infected with HSV-1 (strain KOS, MOI = 5.0 pfu/cell). Virus yields were measured at 32 h PI.
[b]IFN's were pre- and post-treated.

A combination treatment study was also done with IFN alpha and nifedipine. SM cells were pretreated with 2000 U/ml of IFN alpha for 18 h before virus infection. 2000 U/ml of IFN alpha with or without various doses of nifedipine was added after virus infection. Virus yields were measured at 24 h PI. Table 17 shows synergistic effects when IFN alpha was used in combination with 10 or 30 u g/ml of nifedipine.

TABLE 17
Inhibition of HSV Replication by Combined Treatment of IFN alpha and Nifedipine

| Nifedipine[b] (ug/ml) | No IFN alpha | | With IFN alpha | |
|---|---|---|---|---|
| | Virus Yield | Fold Inhibition | Virus Yield[a] | Fold Inhibition |
| 0 | $1.36 \times 10^8$ | | $6.0 \times 10^6$ | 22.7 |
| 3 | $8.75 \times 10^7$ | 1.56 | $8.03 \times 10^6$ | 16.47 |
| 10 | $6.58 \times 10^7$ | 2.07 | $2.45 \times 10^6$ | 55.6 |
| 30 | $4.30 \times 10^7$ | 3.16 | $9.13 \times 10^5$ | 149 |

[a]SM cells were pretreated with 2000 U/ml of IFN alpha for 18 h before virus infection, and then infected with HSV-1 (strain KOS) at a MOI of 4.8 pfu/cells. IFN alpha was post-treated with or without combination with nifedipine. Virus yields were measured at 24 h PI.
[b]Nifedipine was dissolved with PEG 400 to make an initial concentration of 5 mg/ml.

H. Inhibition of Intracellular Free Calcium Response by Papaverine

Until now, the only known pharmacological activity of papaverine was the inhibition of the phosphodiesterase activities associated with the breakdown of cyclic nucleotides. However, the data summarized in FIG. 12 and Table 18 convincingly demonstrate that papaverine inhibits the intracellular free calcium response which is associated with CMV and other viral infections.

Figure 12:
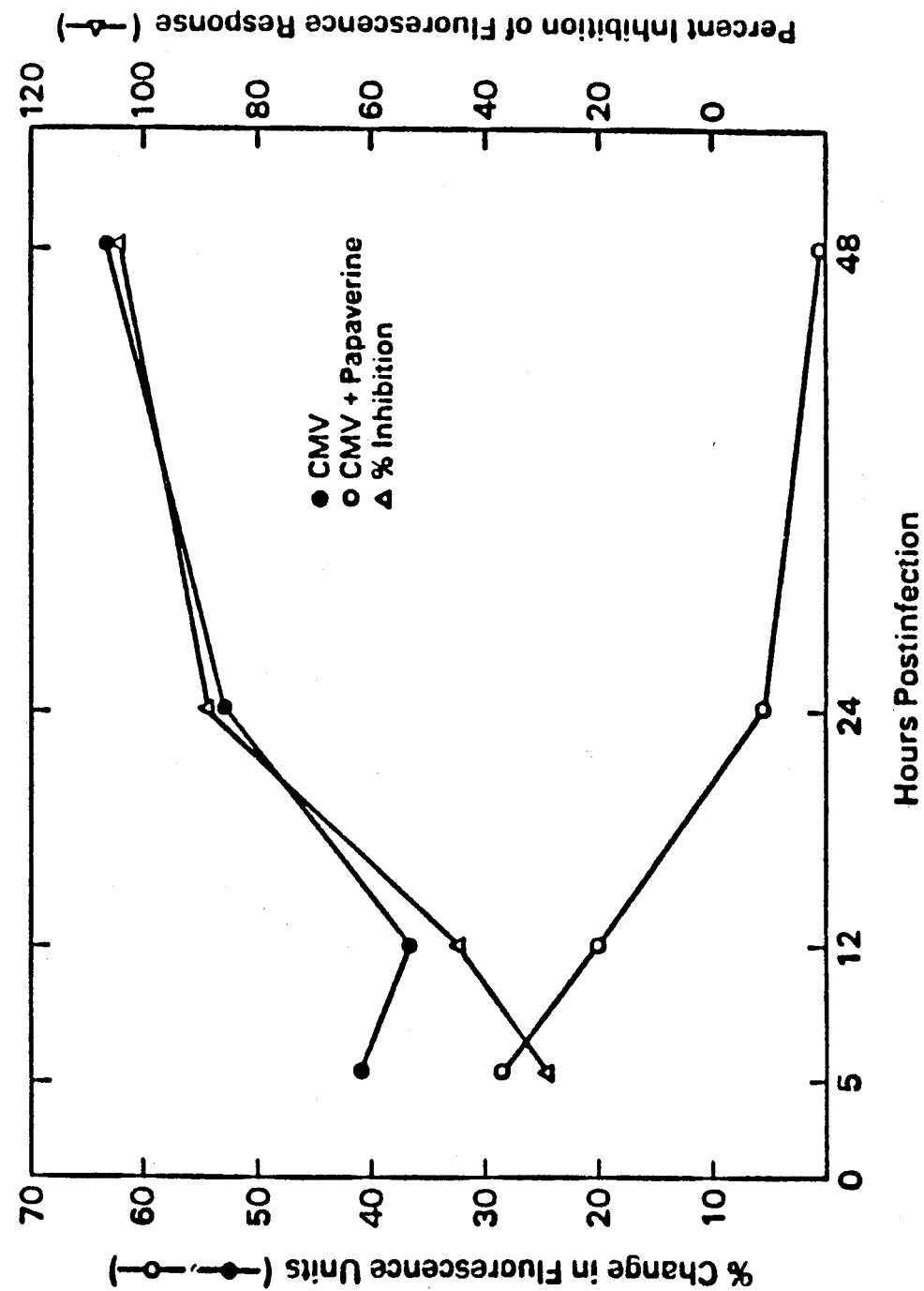
FIG. 12. The effect of papaverine on the CMV-induced enhancement of intracellular free [Ca++] as measured by Quin-2 fluorescence. THY cells grown to confluency in 25 cm² flasks were infected with CMV (strain AD-169; 3 PFU/cell). Intracellular free [Ca++] was measured with the Quin-2 fluorescence assay. CMV-infected cells, not treated with papaverine (●); CMV-infected, papaverine (30 ug/ml)-treated (o); percent inhibition of fluorescence response by papaverine (Δ).

FIG. 12 is a compilation of data from experiments wherein THY cells, grown to confluency in 25 cm[2] flasks, were infected with CMV (strain AD-169; 3 PFU/cell). The intracellular free [Ca++] was measured by Quin-2 fluorescence. As can be seen from the data displayed in FIG. 12, papaverine, when administered to the cells at a concentration of 30 ug/ml, resulted in virtually a 100% inhibition of the fluorescence response by 48 hours post infection. This data has been tabularized in the following table, Table 18.

TABLE 18
Effect of Papaverine on the Intracellular Free [Ca++] in CMV-infected Cells

| | Hour Postinfection | | | | | | | |
|---|---|---|---|---|---|---|---|---|
| | 5 | | 12 | | 24 | | 48 | |
| Sample | Fluorescence Units | % Change | Fluorescence Units | % Change | Fluorescence Units | % Change | Fluorescence Units | % Change |
| Control Cells | 33.6 | | 61.3 | | 42.6 | | 38.6 | |
| CMV-infected Cells | 47.3 | +40.8 | 83.7 | +36.5 | 65 | +52.6 | 63 | +63.2 |
| CMV-infected Cells + Papaverine | 43.3 | +28.9 | 73.7 | +20.2 | 45 | +5.6 | 37.3 | −3.4 |

In further experiments, the effect of papaverine on the intracellular free calcium response was shown to be dose-dependent. For example, Table 19 is a compilation of data which demonstrates the dose-dependent nature of papaverine's effects in this regard. In Table 19 it is shown that upon CMV infection at an MOI of 3.5, a 105% enhancement in the Quin-2 fluorescence was noted. However, treatment with papaverine at 100, 10 and 1 u M concentrations resulted in inhibitions of this fluorescence response of 66, 30 and −3%, respectively, which thus is indicative of a dose dependent effect.

TABLE 19
Dose Response for the Concentration Effect of Papaverine on the CMV-induced IF [Ca++] Response

| CMV[1] | Papaverine | Fluorescence[2] Units | Enhancement[3] (%) | Inhibition of Flourescence Change (%) |
|---|---|---|---|---|
| − | − | 44.5 ± 0.3 | | |
| + | − | 91.0 ± 2.2 | +105 | |
| + | 100 uM | 60.5 ± 1.2 | +36 | 66 |
| + | 10 uM | 77.0 ± 3.9 | +73 | 30 |

TABLE 19-continued

Dose Response for the Concentration Effect of Papaverine on the CMV-induced IF [Ca++] Response

| CMV[1] | Papaverine | Fluorescence[2] Units | Enhancement[3] (%) | Inhibition of Flourescence Change (%) |
|---|---|---|---|---|
| + | 1 uM | 92.5 ± 7.0 | +108 | −3 |

[1]MOI = 3.5 PFU/cell.
[2]Measured at 24 h PI, mean of the determinations for 3 independent cultures processed separately ± standard error of the mean.
[3]Relative to uninfected, untreated cells.

Moreover, as displayed in the following table, Table 20, the data further indicated that this inhibitory effect was exerted when papaverine was added through the first 24 hours after CMV infection.

TABLE 20

Effect of Papaverine Added at Different Times Postinfection on the CMV-induced Intracellular Free [Ca++] Response

| Treatment | | Fluorescence | Enhancement[2] |
|---|---|---|---|
| CMV[3] | Papaverine[4] | units[1] | (%) |
| −[5] | — | 42 ± 1.0 | |
| + | — | 77 ± 0.9 | +83 |
| + | 0 to 48 hr | 56 ± 1.4 | +33 |
| + | 12 to 48 hr | 58 ± 0.7 | +38 |
| + | 24 to 48 hr | 56 ± 3.5 | +33 |

[1]48 h PI; mean of the determinations for 3 independent cultures processed separately, ± standard error of the mean.
[2]Relative to the fluorescence units in uninfected, untreated cells.
[3]Strain AD-169, MOI 3 PFU/cell.
[4]30 ug/ml.
[5]SM cells.

Thus, papaverine inhibition of the intracellular free $CA^{++}$ response is directly associated with papaverine interference of CMV replication. The sensitivity of the $Ca^{++}$ response and CMV replication to inhibition by papaverine were similar. Time of addition studies also support this correlation. Since CMV replication results in yields that are about $10^6$-fold greater than the base level of infectivity, the assay of CMV yields provides for about $10^6$-fold signal for the amplified effect of papaverine on intracellular free [Ca++].

It appears, therefore, that the inhibitory activity of papaverine towards intracellular free Ca++ responses is likely not necessarily the result of its purported cyclic nucleotide modulating activity. First, the replication of cytomegalovirus is extraordinarily sensitive to inhibition by papaverine ($ED_{90}=1.6$ uM), but much less sensitive to inhibition by isobutylmethylxanthine (IBMX) which is reported to have a cyclic nucleotide modulating activity that is similar to papaverine. Second, if inhibition of CMV replication were associated with rising levels of cAMP, as would be the case with papaverine, then forskolin or dibutryl cAMP should have similar inhibitory effect. These two drugs, however, have a much less substantial effect on CMV replication. It could be argued that induction of both cyclic nucleotides was necessary for inhibition of CMV replication.

This possibility was tested with IBMX and cotreatment of injected cels with forskolin and nitroprusside, (which induces higher levels of cGMP) or with both dibutyryl cyclic nucleotides. None of these treatments resulted in an inhibition of CMV replication which was comparable to papaverine's effects. Finally, replication of CMV rather than inhibition of replication of CMV was associated with rising levels of both cAMP and cGMP. Furthermore, papaverine inhibition of CMV replication could be partially reversed by forskolin treatment which also partially reversed the inhibitory effect of papaverine on the CMV-induced increase in cAMP. Thus, the increase in cAMP appears to be specifically associated with CMV replication rather than inhibition of CMV replication.

I. Combination Treatment With Papaverine and DHPG

DHPG is a synthetic nucleoside analog which has been shown to be a potent inhibitor of viral, and in particular CMV, infections. However, DHPG treatment results in various undesirable side effects. Papaverine is also a potent inhibitor of viral infections, but papaverine treatment is not associated with a high frequency of undesirable side-effects. Surprisingly, it has been found that when these two agents are co-administered to viral infected cells, such co-administration exhibits a greatly enhanced antiviral synergistic efficacy. This finding is displayed in Table 21, which is a compilation of data from experiments wherein infected virtually cells were treated with various dose-combinations of the two agents.

As can be seen in Table 21, when DHPG was administered alone at a concentration of 3 uM, a viral inhibition of about 72-fold was observed. Moreover, when papaverine was administered alone at a concentration of 1.5 uM, a viral inhibition of about 8.7-fold was observed. However, when co-administered at these same respective concentrations, a 3000-fold inhibition was observed.

TABLE 21

The Effect of a Combination Treatment of Papaverine and DHPG on CMV Replication[a]

| DHPG (uM) | Papaverine (uM) | | | |
|---|---|---|---|---|
| | 0 | 0.15 | 0.5 | 1.5 |
| 0 | $1.89 \times 10^7$ | $1.35 \times 10^7$ (1.4)[c] | $7.25 \times 10^6$ (2.6) | $2.18 \times 10^6$ (8.7) |
| 0.3 | $1.1 \times 10^7$ (1.7) | $4.93 \times 10^6$ (3.8) | $2.73 \times 10^6$ (6.9) | $3.53 \times 10^5$ (53) |
| 1 | $1.53 \times 10^6$ (12) | $7.50 \times 10^5$ (26) | $2.50 \times 10^5$ (76) | $9.0 \times 10^4$ (210) |
| 3 | $2.63 \times 10^5$ (72) | $1.18 \times 10^5$ (160) | $4.15 \times 10^4$ (450) | $6.30 \times 10^3$ (3000) |

[a]MOI = 3.5 pfu/cell
[b]CMV yields, pfu/ml
[c](Fold inhibition)

From the data displayed in Table 21, it should also be appreciated that lower levels of DHPG, when co-administered with papaverine, have equal or greater activity than the highest level of DHPG when administered alone. This indicates that DHPG doses can be reduced, thus reducing the DHPG-associated toxicities, when co-administered with papaverine.

Moreover, due to the fact that the antiviral nucleoside analogs function by similar mechanisms, papaverine will also prove of benefit when co-administered with other such agents, or their function equivalents or derivatives. For example, papaverine may be co-administered with Ara-C (cytosine arabinoside), Ara-A (adenosine arabinoside), or Acyclovir (acycloguanosine, the parent compound of DHPG), to achieve the benefits afforded by the present invention. Moreover, although the papaverine family members shown in FIG. 11 and Table 13 were not found to have particularly high antiviral activity, dioxyline (Paveril) is one Papaverine family member which is useful in antiviral therapy. Note that, unlike those agents displayed in FIG. 11, dioxyline does have a true isoquinoline ring which is believed to be necessary for antiviral activity. Additionally, another papaverine family agent having an isoquinoline ring and shown to have similar antiviral activity as papaverine is ethaverine, which has the same structure as papaverine except that it includes ethoxy groups in place of the four methoxy groups of papaverine. Therefore, all papaverine family agents having an isoquinoline ring structure are believed to provide the benefits of the present invention.

The findings that the present agents are active in treating virus-infected human tissue culture cells suggest that such agents will prove useful in treating viral infections in man. The agents do not undergo appreciable entero-hepatic metabolism prior to distribution throughout the body, nor do they require metabolism for "activation." Likewise, these viral diseases present similar morphologic changes in infected cells both in vivo and in vitro. For many years, it has been shown that in vitro antiviral activity typically correlates with in vivo activity. In contrast, the main problem has often been the finding of untoward reactions (toxicities) in vivo that were not seen in vitro. Since the present agents are in clinical use, this will not be a problem. Therefore, it is expected that these agents can be administered to an infected patient by all routes presently indicated for their use. It is further expected that topical preparations will be active in treating lesions associated with viral infection of this sort.

The instant invention has been disclosed in connection with standard laboratory procedures used by the applicant. However, it will be apparent to those skilled in the art that variations may be undertaken without departing from the spirit and scope of the invention. More specifically, it will be apparent that certain agents that are both chemically and pharmacologically related may be substituted to achieve the observed antiviral effect. For example, methoxyverapamil and verapamil are virtually indistinguishable pharmacologically as are papaverine and dioxyline and would be expected to give similar results. Additionally, although the present invention is disclosed in terms of activity against CMV and the herpes viruses, it is contemplated that the present agents are effective in treating other viral infections.

These and similar substitutes will be apparent to those skilled in the art and are within the spirit and scope of the invention.

What is claimed is:

1. A method for treating viral infections in an infected host comprising administering to the host a pharmacologically acceptable amount of a papaverine family agent having an isoquinoline ring, together with a pharmacologically acceptable amount of a nucleoside analog, the papaverine family agent and nucleoside analog being administered in amounts sufficient to provide a serum concentration of at least about 0.15 uM and 0.3 uM, respectively.

2. The method of claim 1 wherein the papaverine family agent is papaverine, dioxyline or ethaverine.

3. The method of claim 1 wherein the nucleoside analog is DHPG, Ara-C, Ara-A or Acyclovir.

4. A method for treating viral infections in an infected host comprising administering to the host an effective amount of papaverine and DHPG.

5. A pharmaceutical composition comprising a pharmacologically acceptable amount of a papaverine family agent having an isoquinoline ring, together with a pharmacologically acceptable amount of a nucleoside analog, the papaverine family agent and nucleoside analog being present in the composition in amounts sufficient to provide a serum concentrate of at least about 0.15 uM, and 0.3 uM, respectively, when administered to an infected host.

6. The composition of claim 5 wherein the papaverine family agent is papaverine, dioxyline or ethaverine.

7. The composition of claim 5 wherein the nucleoside analog in DHPG, Ara-C, Ara-A or Acyclovir.

8. A pharmaceutical composition comprising a pharmacologically acceptable amount of papaverine together with a pharmacologically acceptable amount of DHPG, the papaverine and DHPG being present in the composition in amounts sufficient to provide a serum concentrate of at least about 0.15 uM and 0.3 uM, respectively, when administered to an infected host.

* * * * *